United States Patent

Maywald et al.

Patent Number: 5,203,907
Date of Patent: Apr. 20, 1993

[54] ISOXAZOLE- AND ISOTHIAZOLE-5-CARBOXAMIDES

[75] Inventors: Volker Maywald, Ludwigshafen; Peter Muenster, Neulussheim; Hartmann Koenig, Limburgerhof; Gerhard Hamprecht, Weinheim; Thomas Kuekenhoehner, Boehl-Iggelheim; Helmut Walter, Obrigheim; Karl-Otto Westphalen, Speyer; Matthias Gerber, Mutterstadt, all of Fed. Rep. of Germany

[73] Assignee: BASF Aktiengesellschaft, Ludwigshafen, Fed. Rep. of Germany

[21] Appl. No.: 849,256

[22] Filed: Mar. 11, 1992

[30] Foreign Application Priority Data

Mar. 14, 1991 [DE] Fed. Rep. of Germany ....... 4108181

[51] Int. Cl.$^5$ .................. A01N 43/26; C07D 26/06; C07D 275/02
[52] U.S. Cl. .................. 504/191; 548/214; 548/248; 504/269; 504/271; 504/193; 504/196; 504/270
[58] Field of Search .................. 548/214, 248; 71/88, 71/90

[56] References Cited

FOREIGN PATENT DOCUMENTS 3812225 4/1988 Fed. Rep. of Germany ...... 548/248

OTHER PUBLICATIONS

CA 115(3):29302d Preparation of oxazolopyridines Guillaumet et al. p. 775, 1991.

Primary Examiner—Mary C. Lee
Assistant Examiner—Joseph K. McKane
Attorney, Agent, or Firm—Herbert B. Keil

[57] ABSTRACT

Isoxazole- and isothiazole-5-carboxamides of the formula I

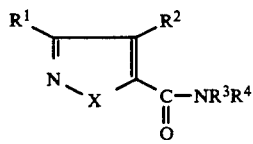

where X is oxygen or sulfur, $R^1$ is halogen, alkylthio, haloalkoxy, haloalkylthio, cyano, formyl, alkanoyl, alkoxycarbonyl, alkylaminocarbonyl, di-$(C_1-C_3)$-alkylaminocarbonyl, cyclopropylaminocarbonyl, methylsulfonyl, trifluoromethylsulfonyl, unsubstituted or substituted phenoxy or phenylthio; $R^2$ is formyl, haloformyl, 4,5-dihydro-2-oxazolyl, $COOR^5$, $COSR^5$ or $CONR^6R^7$, and $R^3$ to $R^7$ have the meanings specified in the description, are suitable as herbicides.

7 Claims, No Drawings

ISOXAZOLE- AND ISOTHIAZOLE-5-CARBOXAMIDES

The present invention relates to carboxamides of the formula I

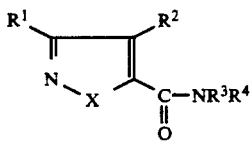

where
X is oxygen or sulfur;
$R^1$ is halogen,
$C_1$-$C_4$-alkylthio, $C_1$-$C_4$-haloalkoxy, $C_1$-$C_4$-haloalkylthio, cyano, formyl, $C_2$-$C_4$-alkanoyl, $C_1$-$C_4$-alkoxycarbonyl, $C_1$-$C_4$-alkylaminocarbonyl, di-($C_1$-$C_3$)-alkylaminocarbonyl, cyclopropylaminocarbonyl, methylsulfonyl or trifluoromethylsulfonyl;
phenoxy or phenylthio, which can be substituted up to three times by $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano or nitro;
$R^2$ is formyl, haloformyl, 4,5-dihydro-2-oxazolyl, $COYR^5$ or $CONR^6R^7$, where
Y is oxygen or sulfur;
$R^5$ is hydrogen; $C_1$-$C_6$-alkyl which can carry 1 to 5 halogens and/or up to three hydroxyl and/or $C_1$-$C_4$-alkoxy groups and/or one of the following:
cyano,
$C_1$-$C_4$-alkoxy-$C_2$-$C_4$-alkoxy,
$C_1$-$C_3$-alkylthio,
$C_1$-$C_3$-alkylamino, di-($C_1$-$C_3$)-alkylamino, $C_3$-$C_6$-cycloalkylamino or di-($C_3$-$C_6$)-cycloalkylamino, trimethylsilyl,
$C_1$-$C_3$-alkylsulfinyl or $C_1$-$C_3$-alkylsulfonyl,
carboxyl, $C_1$-$C_3$-alkoxycarbonyl, $C_1$-$C_3$-alkoxycarboxyl-$C_1$-$C_3$-alkoxy or $C_1$-$C_3$-alkoxycarbonyl-$C_1$-$C_3$-alkoxy-$C_1$-$C_3$-alkoxycarbonyl,
di-($C_1$-$C_3$)-alkylaminocarbonyl,
di-($C_1$-$C_3$)-alkoxyphosphonyl,
$C_1$-$C_6$-alkaniminoxy or $C_5$-$C_6$-cycloalkaniminoxy,
N-phthalimido, N-succinimido, benzyloxy, benzoyl, it being possible for these cyclic radicals additionally to carry one to three of the following: halogen, $C_1$-$C_3$-alkyl or $C_1$-$C_3$-alkoxy,
a 5- or 6-membered saturated heterocyclic radical or a 5- or 6-membered heteroaromatic radical with, in each case, up to 3 hetero atoms selected from the group comprising oxygen, sulfur and nitrogen, where two oxygen and/or sulfur atoms must not be directly adjacent and where the heterocycles can also carry one or two of the following substituents: halogen, $C_1$-$C_3$-alkyl, $C_1$-$C_3$-alkoxy or $C_1$-$C_3$-alkoxycarbonyl;
phenyl which can also carry up to three of the following substituents: halogen, nitro, cyano, $C_1$-$C_3$-alkyl, partially or completely halogenated $C_1$-$C_3$-alkyl, $C_1$-$C_3$-alkoxy or partially or completely halogenated $C_1$-$C_3$-alkoxy or $C_1$-$C_2$-alkoxycarbonyl;
—$CR^{10}$=N—$R^{11}$ where
$R^{10}$ is hydrogen or $C_1$-$C_6$-alkyl and
$R^{11}$ is $C_1$-$C_6$-alkoxy, $C_3$-$C_6$-alkenyloxy or $C_3$-$C_6$-alkynyloxy, each of which can carry 1 to 3 halogens and/or one phenyl with, if required, up to three of the following: halogen, nitro, cyano, $C_1$-$C_3$-alkyl, $C_1$-$C_3$-alkoxy; phenoxy which can also carry up to three of the following substituents: halogen, nitro, cyano, $C_1$-$C_3$-alkyl or $C_1$-$C_3$-alkoxy; $C_1$-$C_6$-alkylamino, di-($C_1$-$C_3$)-alkylamino or phenylamino where the phenyl can additionally carry up to three of the following: halogen, nitro, cyano, $C_1$-$C_3$-alkyl or $C_1$-$C_3$-alkoxy;
$R^5$ is also $C_3$-$C_8$-cycloalkyl;
$C_3$-$C_6$-alkenyl, $C_3$-$C_6$-cycloalkenyl or $C_3$-$C_6$-alkynyl, it being possible for these radicals to carry one of the following groups: hydroxyl, halogen, $C_1$-$C_4$-alkoxy or phenyl, the latter possibly carrying one to three of the following groups: halogen, nitro, cyano, $C_1$-$C_4$-alkyl, partially or completely halogenated $C_1$-$C_4$-alkyl or $C_1$-$C_4$-alkoxy;
phenyl which can carry one to three of the following groups: halogen, nitro, cyano, $C_1$-$C_4$-alkyl, partially or completely halogenated $C_1$-$C_4$-alkyl, $C_1$-$C_4$-alkoxy, partially or completely halogenated $C_1$-$C_4$-alkoxy or $C_1$-$C_4$-alkoxycarbonyl;
a five- or six-membered heterocyclic radical with up to three hetero atoms selected from the group comprising oxygen, sulfur and nitrogen, where two oxygen and/or sulfur atoms must not be directly adjacent and where the heterocycles can also carry one or two of the following substituents: halogen, $C_1$-$C_3$-alkyl, $C_1$-$C_3$-alkoxy or $C_1$-$C_3$-alkoxycarbonyl;
benzotriazolyl;
N-phthalimido, tetrahydrophthalimido, succinimido, maleimido;
2,2-dimethyl-1,3-dioxolan-4-ylmethyl or 1,3-dioxolan-2-on-4-ylmethyl;
where Y is O: one equivalent of a cation from the group comprising alkali and alkaline earth metals, manganese, copper, iron, ammonium and ammonium substituted by up to 4 $C_1$-$C_3$-alkyl groups; or
—N=$CR^8R^9$ where
$R^8$ and $R^9$ are each hydrogen; $C_1$-$C_4$-alkyl which can be unsubstituted or partially or completely halogenated and can carry a $C_1$-$C_3$-alkoxy or phenyl radical, it being possible for the latter in turn to be substituted one to three times by halogen, nitro, cyano, $C_1$-$C_3$-alkyl, partially or completely halogenated $C_1$-$C_3$-alkyl, $C_1$-$C_3$-alkoxy or partially or completely halogenated $C_1$-$C_3$-alkoxy; $C_3$-$C_6$-cycloalkyl; $C_1$-$C_4$-alkoxy; furanyl or phenyl, which can additionally carry up to three of the following substituents: halogen, nitro, cyano, $C_1$-$C_3$-alkyl, partially or completely halogenated $C_3$-$C_3$-alkyl, $C_1$-$C_3$-alkoxy or partially or completely halogenated $C_1$-$C_3$-alkoxy; or
$R^8$ and $R^9$ together form a methylene chain with 4 to 7 members;
—W—Z where W is a $C_3$-$C_4$-alkylene chain, an ethoxyethylene chain, a 2-butenylene or a 2-butynylene chain, and Z is a moiety which is bonded in the ω-position to W and is the same moiety which is linked to W in the α-position of W;
$R^6$ is hydrogen, $C_1$-$C_6$-alkyl or $C_3$-$C_8$-cycloalkyl and
$R^7$ is hydrogen, $C_1$-$C_6$-alkyl, —C($OR^{12}$)=N—H or —C($OR^{12}$)=—($C_1$-$C_4$)-alkyl, where $R^{12}$ is $C_1$-$C_4$-alkyl, or
$R^6$ and $R^7$ together form a methylene chain with 4 to 5 members;
$R^3$ is hydrogen;

$C_1$–$C_6$-alkyl which can carry one to three of the following substituents hydroxyl, halogen, $C_1$–$C_4$-alkoxy, $C_1$–$C_4$-alkylthio or di-($C_1$–$C_4$)-alkylamino;

$C_3$–$C_8$-cycloalkyl which can be substituted one to three times by halogen, $C_1$–$C_4$-alkyl and partially or completely halogenated $C_1$–$C_4$-alkyl, $R^4$ is hydrogen; hydroxyl, $C_1$–$C_4$-alkoxy;

$C_1$–$C_6$-alkyl which can carry one to three of the following: halogen, cyano, $C_1$–$C_4$-alkoxy, partially or completely halogenated $C_4$–$C_4$-alkoxy, $C_1$–$C_4$-alkylthio, partially or completely halogenated $C_4$–$C_4$-alkylthio, di-$C_1$–$C_4$-alkylamino, $C_3$–$C_8$-cycloalkyl or phenyl, it being possible for the latter in turn to carry one to three of the following: halogen, cyano, nitro, $C_1$–$C_4$-alkyl, partially or completely halogenated $C_1$–$C_4$-alkyl, $C_1$–$C_4$-alkoxy, $C_1$–$C_4$-alkylthio, or partially or completely halogenated $C_1$–$C_4$-alkoxy or $C_1$–$C_4$-alkylthio;

$C_3$–$C_8$-cycloalkyl which can carry one to three of the following: halogen, nitro, cyano, $C_1$–$C_6$-alkyl, partially or completely halogenated $C_1$–$C_6$-alkyl, $C_1$–$C_4$-alkoxy or partially or completely halogenated $C_1$–$C_4$-alkoxy;

$C_3$–$C_6$-alkenyl whose double bond can be epoxidized, or $C_3$–$C_6$-alkynyl, each of which can be substituted one to three times by halogen and/or once by phenyl which in turn can carry one to three of the following groups: $C_1$–$C_4$-alkyl, $C_1$–$C_4$-haloalkyl, $C_1$–$C_4$-alkoxy, $C_3$–$C_4$-haloalkoxy, $C_1$–$C_4$-alkylthio, $C_1$–$C_4$-haloalkylthio, halogen, cyano or nitro; di-($C_1$–$C_4$)-alkylamino;

a 5- to 6-membered heterocyclic saturated or aromatic radical with one or two hetero atoms selected from the group comprising oxygen, sulfur and hydrogen, which can be substituted once to three times by $C_1$–$C_4$-alkyl or halogen;

phenyl which can carry one to four of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, nitro, cyano, formyl, $C_2$–$C_4$-alkanoyl, $C_2$–$C_4$-haloalkanoyl or $C_1$–$C_4$-alkoxycarbonyl; naphthyl which can be substituted once to three times by $C_1$–$C_4$-alkyl or halogen; or $R^3$ and $R^4$ together form a methylene chain with 4 to 7 members, which can be interrupted by oxygen, sulfur or N-methyl, or —(CH$_2$)$_3$—CO— and the environmentally compatible salts of the compounds I.

The present invention also relates to herbicidal agents which contain the compounds I as active substances and to processes for preparing the compounds I.

Herbicidal isoxazole- and isothiazole-5-carboxamides and their derivatives have been disclosed, eg. in DE-A 38 12 225.

It is an object of the present invention, despite the intrinsically satisfactory herbicidal activity of these compounds, to provide similar compounds with improved crop selectivity.

We have found that this object is achieved by the isoxazole- and isothiazole-5-carboxamides defined above.

The carboxamides of the formula I according to the invention can be prepared in a variety of ways, preferably by the following processes:

1 One process for synthesizing the novel isoxazole- and isothiazole-5-carboxamides of the formula I where $R^2$ is carboxyl starts from dialkyl isoxazole- and isothiazole-4,5-dicarboxylates of the formula II with various substituents in position 3. The latter are initially hydrolyzed with one equivalent of an aqueous base to the monocarboxylic acids III which are converted in a conventional manner into the halides IV or other activated forms of the carboxylic acid and subsequently amidated with an amine Va. The ester moiety in position 4 is then hydrolyzed in a conventional manner. This process has been described in detail in DE-A 38 12 225.

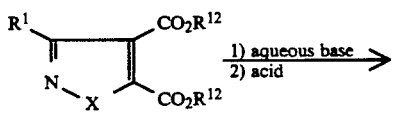

II
($R^{12} = C_1$–$C_4$-Alkyl)

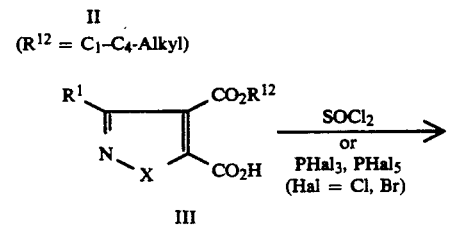

III

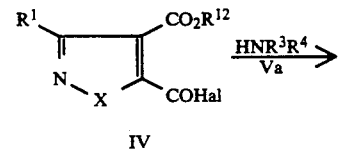

IV

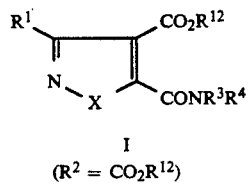

I
($R^2 = CO_2R^{12}$)

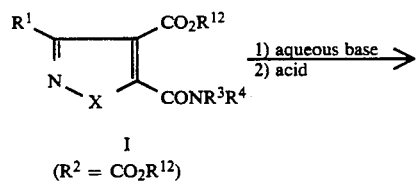

I
($R^2 = CO_2R^{12}$)

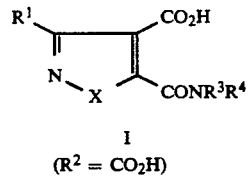

I
($R^2 = CO_2H$)

Esterification of the carboxylic acid (I with $R^2$=$CO_2H$) or halogenation in a conventional manner results in the corresponding acid derivatives.

The dialkyl isoxazole- or isothiazole-4,5-dicarboxylates II required for this process however are known from the literature, can be prepared by ways known from the literature or can be obtained, for example, in the following ways:

a) Process for preparing dialkyl isoxazole-4,5-dicarboxylates of the formula II where $R^1$ is halogen comprises reacting a dihaloformaldoxime VI, preferably dibromo- or dichloroformaldoxime, in the presence of a base with dialkyl acetylenedicarboxylates VII to give the corresponding 3-haloisoxazole-4,5-dicarboxylic diesters II. The procedure for this is preferably such that the dihaloformaldoxime VI is added in a solvent dropwise to a mixture of from one to ten equivalents of dialkyl acetylenedicarboxylate VII and of a base, likewise in a from one- to ten-fold molar excess and likewise dissolved in a solvent, a mixture of solvents or a two-phase system composed of an organic solvent and water, and working up is carried out after a reaction time of from two to twenty hours.

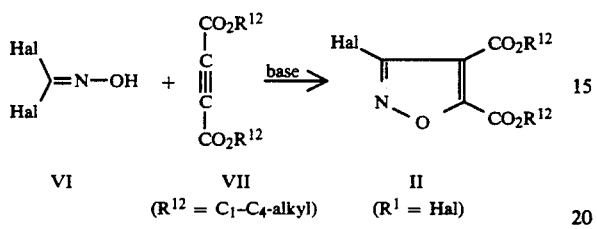

VI     VII     II
($R^{12}$ = $C_1$–$C_4$-alkyl)    ($R^1$ = Hal)

Examples of suitable solvents for this reaction are alcohols such as methanol, ethanol, propanol or isopropanol, ethers such as diethyl ether, methyl tert-butyl ether, tetrahydrofuran or dioxane, hydrocarbons such as pentane, hexane, cyclohexane, petroleum ether or naphtha, aliphatic halohydrocarbons such as methylene chloride, chloroform, tetrachloromethane, dichloroethane, trichloroethane, tetra- or hexachloroethane, aromatic compounds such as benzene, toluene, xylenes or chlorobenzenes, esters such as ethyl acetate, and formamide, N-methllpyrrolidone, dimethyl sulfoxide and sulfolane.

The reaction can be carried out at from −15° C. to the boiling point of the solvent, and the range from 0° to 40° C. is particularly preferred. The reaction can also be carried out under elevated pressure, but atmospheric pressure is preferred.

Suitable bases are organic compounds such as aliphatic or aromatic amines or pyridines, but inorganic compounds such as the carbonates and bicarbonates of the alkali metals and alkaline earth metals are preferred.

The aldoximes required for this process are known (D. M. Vyas, Y. Chiang, T. W. Doyle, Tetrahedron Lett. 25 (1984) 387, K. Hallig, I. Thomsen, K. B. G. Torssell, Liebigs Ann. Chem. (1989) 985–990).

b) Dialkyl isoxazole-4,5-dicarboxylates of the formula II where $R^1$ is cyano, $C_1$–$C_4$-alkylthio, unsubstituted or substituted phenoxy or unsubstituted or substituted phenylthio are obtained, for example, by reacting a dialkyl haloisoxazole-4,5-dicarboxylate of the formula II where $R^1$ is chlorine or bromine with cyanide ions or with alcoholates or thiolates of the formula IX. The procedure for this is expediently such that anions of the type IX are generated with a suitable base in an inert aprotic polar solvent from the corresponding alcohols or thiols VIII $R^{13}XH$                      VIII where X is O or S, and $R^{13}$ is $C_1$–$C_4$-alkylthio, unsubstituted or substituted phenoxy or unsubstituted or substituted phenylthio, and are then reacted with a dialkyl 3-haloisoxazole-4,5-dicarboxylate II in an inert dipolar aprotic solvent. The sequence of addition is arbitrary but the anion in solution is usually added dropwise to the diester. The reaction is generally carried out at from −20° C. to the boiling point of the solvent, preferably from 0° to 50° C.

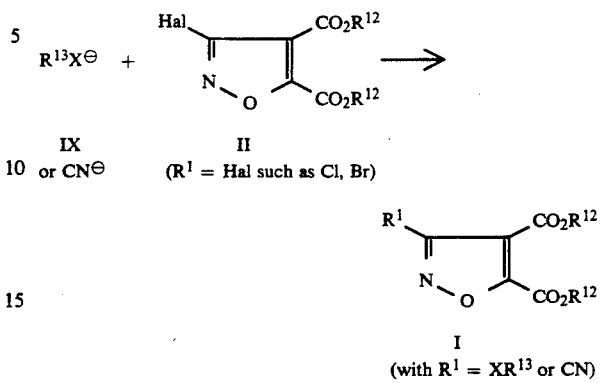

Examples of suitable solvents are ethers such as diethyl ether, tert-butyl methyl ether, tetrahydrofuran, dioxane and 1,2-dimethoxyethane.

Suitable bases for liberating the anion IX are alkali metal hydrides such as sodium and potassium hydrides, alkali metal derivatives of hydrocarbons such as n-butyllithium, tertbutyllithium, methyllithium and phenyllithium or, preferably for more acidic alcohols or thiols, amines such as triethylamine, pyridine, ethyldicyclohexylamine, 1,4-diazabicyclo[2.2.2]octane (DABCO) or 1,8-diazabicyclo[5.4.0]undec-7-ene (DBU).

The components (alcohol, thiol, cyanide), base and dialkyl 3-haloisoxazole-4,5-dicarboxylate, are preferably used in the ratio 1:1:1.

c) Dialkyl isoxazole-4,5-dicarboxylates of the formula II where $R^1$ is methylsulfonyl or trifluoromethylsulfonyl are obtained, for example, by oxidizing a dialkyl isoxazole-4,5-dicarboxylate of the formula II where $R^1$ is methylthio or trifluoromethylthio. The conversion of thioethers into sulfones with oxidizing agents such as $H_2O_2$, peracids, ozone, potassium permanganate, ruthenium tetroxide etc. is a generally known reaction (A. C. Cope, D. E. Morrison, L. Field, J. Am. Chem. Soc. 72 (1950) 59; C. G. Overberger et al., J. Am. Chem. Soc. 72 (1950) 2856; B. R. Baker, M. V. Querry, A. F. Kadish, J. Org. Chem. 15 (1950) 402; S. J. Daum, R. L. Clarke, THL (1967) 165; C. Djerassi, R. R. Engle, J. Am. Chem. Soc. 75 (1953) 3838; J. Goerdeler, M. Budnowski, Ber. Deutsch. Chem. Ges. 94 (1961) 1682; Jerry March, Advanced Organic Chemistry, Third Edition, John Wiley & Sons 1985, p. 1089).

d) A very widely applicable process for synthesizing various substituted dimethyl isoxazole-4,5-dicarboxylates of the formula II where $R^1$ is, for example, hydrogen, unsubstituted or substituted alkyl, cycloalkyl, alkenyl, cycloalkenyl, alkynyl, phenyl or heterocyclvl- comprises reacting an appropriately substituted aldoxime of the formula X with dialkyl acetylenedicarboxylate VII in the presence of hypohalite. The hypohalite oxidizes the aldoxime X to the corresponding nitrile oxide. The nitrile oxide is a reactive 1,3-dipole which undergoes a cycloaddition with the dipolarophile dialkyl acetylenedicarboxylate VII present in the reaction medium.

It is expedient to react equimolar amounts of the aldoxime X and of the acetylenedicarboxylic diester VII with the hypohalite. The hypohalite can be added to the reaction mixture in stoichiometric amount but, as a rule, a slight excess, up to a two-fold excess, is added to the reaction mixture. It may be advantageous, for technical reasons, to limit the conversion by using less than stoichiometric amounts of hypohalite, eg. from 50 to 90 mol-% of hypohalite relative to X. It is likewise possible to use less than or more than stoichiometric amounts of the reactants X or VII.

The hypohalites generally used are hypobromites or hypochlorites, preferably the latter It is possible to employ for this purpose aqueous solutions of hypochlorous or hypobromous acid, but alkali metal or alkaline earth metal hypochlorites or hypobromites, eg. sodium hypochlorite, potassium hypochlorite, calcium hypochlorite, magnesium hypochlorite, strontium hypochlorite, barium hypochlorite and the corresponding hypobromites are preferably used. Sodium, potassium and calcium hypochlorite are particularly preferred, specifically in the form of their commercially available aqueous solutions.

Examples of suitable solvents for the process are alcohols such as methanol, ethanol, propanol or isopropanol, ketones such as acetone or methyl ethyl ketone, ethers such as diethyl ether, methyl tert-butyl ether, tetrahydrofuran or dioxane, hydrocarbons such as pentane, hexane, cyclohexane, petroleum ether, white oils or naphtha, aliphatic halohydrocarbons such as methylene chloride, chloroform, tetrachloromethane, dichloroethane, trichloroethane, tetrachloroethane or perchloroethane, aromatic compounds such as benzene, toluene, xylenes or chlorobenzenes, esters such as ethyl acetate, and dimethylformamide, N-methylpyrrolidone, dimethyl sulfoxide, sulfolane etc.

The reaction can be carried out in a wide range of temperatures. It usually takes place at $-15°$ C. or below, and the upper temperature limit is in principle determined only by the boiling point of the solvent because the reaction is expediently carried out under atmospheric pressure. The reaction is preferably carried out at from 0° to 40° C. and can also be carried out under elevated pressure, especially under autogenous pressure.

The aldoximes X required for this process are known or can be prepared by conventional processes (eg. Houben-Weyl, Methoden der organischen Chemie, Vol. 10/4, pages 55-56, Thieme Verlag, Stuttgart 1968) by reacting the corresponding aldehydes with hydroxylamine. The aldoximes X can, of course, be used both in the form of their E or Z isomers and as mixtures of these stereoisomers. The acetylenedicarboxylic diesters VII are commercially available or can be prepared by conventional methods (eg. Organic Syntheses Coll. Vol. 4, 329).

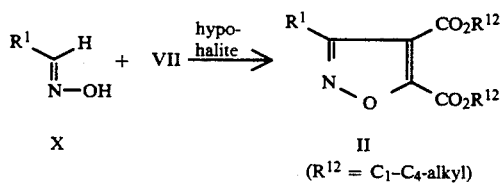

e) Dimethyl isoxazole-4,5-dicarboxylates of the formula II where R is hydroxymethyl and $R^{12}$ is methyl are obtained by firstly carrying out the cycloaddition of an aldoxime of the formula X where $R^1$ is acetox-ymethyl with dimethyl acetylenedicarboxylate VII ($R^{12}$=methyl) in the presence of sodium hypochlorite under the conditions described in d) and then removing the acetoxy group by hydrolysis. The procedure for this is expediently such that the dimethyl acetoxymethylisoxazole-4,5-dicarboxylate II ($R^1$=acetoxymethyl) is dissolved in methanol and then sodium methylate is added from 1 to 2 time the molar amount. The reaction is carried out at from 20° to 65° C.

f) The formyl- or carboxyl-substituted compounds can be obtained from the dimethyl hydroxymethylisoxazole-4,5-dicarboxylates by oxidizing the hydroxymethyl group (Jerry March, Advanced Organic Chemistry, Third Edition, John Wiley & Sons 1985, pp. 1048-1120). The carboxyl group can subsequently be converted in a conventional manner into $C_1$-$C_3$-alkoxycarbonyl, $C_1$-$C_3$-aminocarbonyl or di-($C_1$-$C_3$)-alkylaminocarbonyl.

2. Another process for preparing compounds of the formula I where $R^1$ is $C_1$-$C_4$-alkylthio, cyano, unsubstituted or substituted phenoxy or unsubstituted or substituted phenylthio and $R^2$ is carboxyl or formyl comprises amidating the 3-chloroisoxazole-5-carboxylic acid XI by conventional methods and reacting the resulting amides XII, after replacement of chloride by an appropriate nucleophilic group, with a carboxylating or formylating reagent in the presence of a base in a conventional manner (cf. DE-A 38 12 225). The nucleophilic replacement of chloride is carried out under the conditions described above in 1 b).

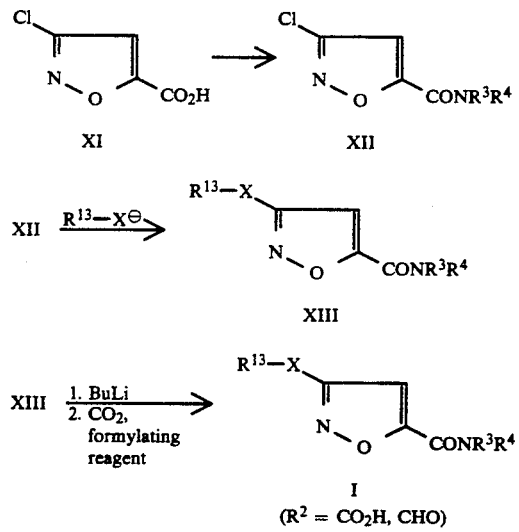

3. Compounds of the formula I $R^2$ is COHal are obtained, for example, by reacting a carboxylic acid of the formula I where $R^2$ is COOH in a conventional manner with an inorganic acid chloride such as thionyl chloride or phosphorus trihalides or pentahalides, expediently employing from 1 to 5 mole equivalents, preferably 1 to 2 mole equivalents, of the latter. The reaction can be carried out without solvent or in the presence of an inert organic solvent such as benzene or toluene at from room temperature to the boiling point of the inorganic acid halide or of the inert organic solvent. Addition of a catalyst such as dimethylformamide or 4-dimethylaminopyridine may be advantageous in some cases.

After the reaction is complete, the acid halide can be isolated in a conventional manner, eg. by removing the excess inorganic acid chloride and the organic solvent by distillation.

4. Compounds of the formula I where $R^2$ is formyl are obtained in a conventional manner by reducing the alkyl carboxylate I ($R^2$=$CO_2R^{12}$) (L. I. Zakharkin, I. M. Khorlina, Tetrahedron Lett. (1962) 619, C. Szantay, L. Toke, P. Kolonits, J. Org. Chem. 31 (1966) 1447, R. Kanazawa, T. Tokoroyama, Synthesis (1976) 526), or the carbonyl halide (Y. Watanabe et al., Bull. Chem. Soc. Jpn 44 (1971) 2569, D. G. Smith, D. J. H. Smith, J. C. S. Chem. Commun. (1975) 459, R. Grewe, H. Buttner, Ber. Deutsch. Chem. Ges. 91 (1958) 2452, Jerry March, Advanced Organic Chemistry, Third Edition, John Wiley & Sons 1985, pp. 1048-1120).

5. Compounds of the formula I where $R^2$ is $COYR^5$ or $CONR^6R^7$ are obtained, for example, by reacting a carboxylic acid I ($R_2$=COOH) with an alcohol or thiol XIV or an amine Vb in the presence of a water-abstracting agent, eg. propanephosphonic anhydride (PPA) or dicyclohexylcarbodiimide (DCC) at from $-20°$ to $70°$ C., preferably $0°$ to $60°$ C. The precursors are advantageously reacted in approximately stoichiometric amounts, preferably in the presence of an inert solvent such as tetrahydrofuran, dichloromethane, toluene or ethyl acetate.

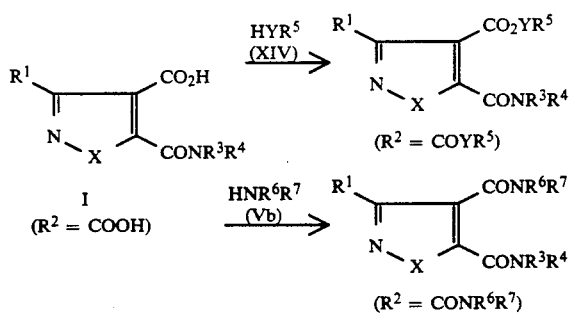

6. Another process for preparing compounds of the formula I where $R^2$ is $COYR^5$ or $CONR^6R^7$ is based on reacting an acid halide of the formula I ($R^2$=COHal) in a conventional manner with an alcohol or thiol XIV or with an amine of the formula Vb. The procedure for this is expediently such that the acid halide I is dissolved in an inert organic solvent and a base is added dropwise and then the alcohol XIV, the thiol XIV or the amine Vb, preferably likewise dissolved in an inert organic solvent, is likewise added dropwise. The reaction is generally complete after from 1 to 12 hours. The mixture can be worked up in a conventional manner, for example by hydrolysis with water and extraction of the final product with an organic solvent.

Suitable solvents are diethyl ether, methyl tert-butyl ether, tetrahydrofuran and dioxane, halohydrocarbons such as dichloromethane, chloroform, 1,2-dichloroethane and chlorobenzene or aromatic compounds such as benzene, toluene and xylenes.

The reaction can be carried out at from $-10°$ to $50°$ C., preferably $0°$ to $30°$ C.

Preferably used as base is a tertiary amine such as pyridine, N,N-dimethylaniline or triethylamine.

The amines Vb required for processes 5 and 6 are known or can be prepared by known processes. The alcohols and thiols $HYR^5$ XIV are known in some cases. If $R^5$ is $C_3$-$C_6$-alkyl substituted by $-CR^{10}=NR^{11}$, these alcohols and thiols can be prepared by one of the following processes (shown by way of example for Y=O and $R^5$=$CH_2CH$=$NOC_2H_5$):

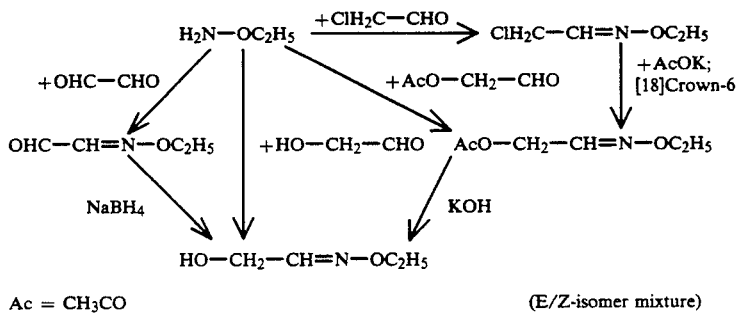

The following alcohols have been prepared, for example, by these processes: HO—$CH_2$—CH=N—$OCH_2$, HO—$CH_2$—$C(CH_3)$=N—$OCH_3$, HO—$CH_2$—CH=N—$OCH_2$—CH=CHCl, HO—$CH_2$—CH=N—$OCH_2$—$C_6H_5$, HO—$CH_2$—$C(CH_3)$=N—$OC_2H_5$, HO—$CH_2$—CH=N—$OCH_2$—CH=$CH_2$, HO—$CH_2$—$C(CH_3)$=N—$OCH_2$—$C_6H_5$, HO—$CH_2$—$C(CH_3)$=N—$OCH_2CH$=$CH_2$.

7. One process according to the invention for preparing compounds of the formula I where $R^5$ is $C_1$-$C_6$-alkyl which is substituted by $-CR^{10}=N-R^{11}$ comprises dissolving an isoxazole- or isothiazole-4-carboxylic acid of the formula I in an aprotic polar organic solvent, converting it with a base into the salt and subsequently reacting with about one equivalent of a substituted alkyl chloride XV (where A is branched or unbranched $C_1$-$C_6$-alkyl). The reaction is generally complete after 4 to 20 hours and working up is possible in a conventional manner by adding water and extracting the product with an organic solvent. The reaction can be carried out at from $0°$ to $100°$ C., preferably $20°$ to $60°$ C. A particularly suitable solvent is dimethyl sulfoxide.

Suitable bases are carbonates and alcoholates of the alkali metals and alkaline earth metals, especially potassium carbonate and potassium tert-butylate.

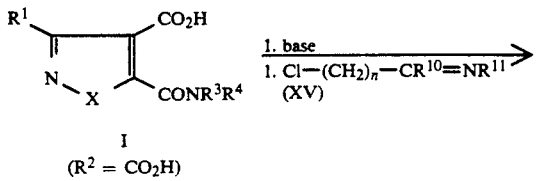

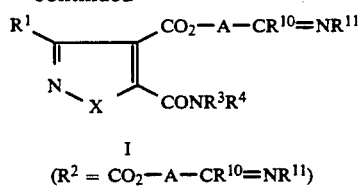

I
($R^2 = CO_2-A-CR^{10}=NR^{11}$)

8. Compounds of the formula I where $R^2$ is $COOR^5$ where $R^5$ is a cation such as alkali metal, alkaline earth metal or ammonium are obtained by reacting a substituted isoxazole- or isothiazole-4-carboxylic acid I with one equivalent of the cation. If the cation is inorganic, such as sodium, potassium or calcium, the acid I is expediently dissolved or suspended in water or a lower alcohol, and one equivalent of the cation is added. The cation can be employed, for example, in the form of its hydroxide, carbonate or bicarbonate, preferably its hydroxide. The reaction is generally complete after a few minutes, and working up is possible in a conventional manner, eg. by precipitation and filtration with suction or by concentration of the solution. Ammonium salts are prepared by dissolving or suspending the acid I in an organic solvent such as diethyl ether, tetrahydrofuran or dioxane and treating the mixture with one equivalent of ammonia, an amine or a tetraalkylammonium hydroxide.

Amines which can be employed include the following: methylamine, ethylamine, n-propylamine, isopropylamine, n-butylamine, isobutylamine, secbutylamine, n-amylamine, isoamylamine, hexylamine, heptylamine, octylamine, nonylamine, decylamine, undecylamine, dodecylamine, tridecylamine, tetradecylamine, pentadecylamine, hexadecylamine, heptadecylamine, octodecylamine, methylethylamine, methylisopropylamine, methylhexylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, diheptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, 2-butenylamine, 2-pentenylamine, 2,3-dimethyl-2-butenylamine, di-2-butenylamine, 2-hexenylamine, propylenediamine, tallow amine, cyclopentylamine, cyclohexylamine, dicyclohexylamine, piperidine, morpholine and pyrrolidine.

Examples of tetraalkylammonium hydroxides which can be used are tetramethyl-, tetraethyl- and trimethylbenzylammonium hydroxide. As a rule, the ammonium salt or organic ammonium salt precipitates from the solution and can be isolated by conventional methods. Alternatively, the salt can also be obtained by evaporating the solvent.

9. Compounds of the formula I where $R^2$ is 4,5-dihydro-2-oxazolyl can be obtained by conventional reaction of carboxamides of the formula I where $R^2$ is COOH or $COOR^{12}$ with an amino alcohol of the formula XVI (cf. Theodora W. Greene, Protective Groups in Org. Synthesis, John Wiley & Sons, p. 185 (1981)).

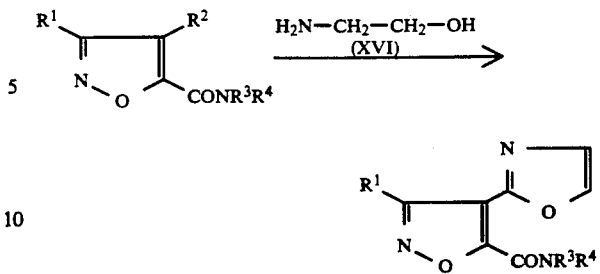

The reaction is carried out by heating the compounds at from 0° to 180° C., preferably under reflux, with an amino alcohol XVI, in the presence or absence of an inert solvent. The ester or carboxylic acid and amino alcohol XVI are employed in the ratio from 1:1 to 1:2.5, preferably 1:1 to 1:1.5. The reaction is generally carried out under atmospheric pressure or the autogenous pressure of the solvent.

Solvents expediently used are halohydrocarbons such as chlorobenzene and 1,2-dichlorobenzene, ethers, eg. methyl tert-butyl ether, 1,2-dimethoxyethane, diethylene glycol dimethyl ether, tetrahydrofuran and dioxane, alcohols such as methanol, ethanol, propanol or ethylene glycol, dipolar aprotic solvents, eg. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolin-2-one or aromatic compounds, eg. benzene, toluene and xylene. The concentration of the precursors in the solvent is generally from 0.1 to 5 mol/l, preferably 0.2 to 2 mol/l.

The reaction is generally complete after 14 hours; the carboxamides I ($R^2=$4,5-dihydro-2-oxazolyl) are then, where appropriate, precipitated by adding water and filtered off with suction, or extracted with an organic solvent and purified by conventional methods such as recrystallization or chromatography.

The substituents in the compounds I according to the invention have the following meanings, for example:

X is oxygen or sulfur;

$R^1$ is halogen such as fluorine, chlorine, bromine and iodine, especially chlorine and bromine;

$C_1-C_4$-alkylthio such as methylthio, ethylthio, propylthio, 1-methylethylthio, n-butylthio, 1-methylpropylthio, 2-methylpropylthio and 1,1-dimethylethylthio, especially methylthio and ethylthio, $C_1-C_4$-haloalkoxy such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, especially trifluoromethoxy and pentafluoroethoxy, $C_1-C_4$-haloalkylthio such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio and pentafluoroethylthio, especially trifluoromethylthio and pentafluoroethylthio, cyano, formyl, $C_1-C_4$-alkanoyl such as ethanoyl, propanoyl, 2-methylpropanoyl, butanoyl, especially ethanoyl (acetyl) and 2-methylpropanoyl, $C_1$-$C_4$-alkoxycarbonyl such as methoxycarbonyl, ethoxycarbonyl, propoxycarbonyl, 1-methylethoxycarbonyl, butoxycarbonyl and 1,1-dimethylethoxycarbonyl, especially methoxycarbonyl, $C_1$-$C_4$-alkylaminocarbonyl such as methylaminocarbonyl, ethylaminocarbonyl, propylaminocarbonyl, 1-methylethylaminocarbonyl, butylaminocarbonyl, 1,1-dimethylethylaminocarbonyl, especially methylaminocarbonyl, ethylaminocarbonyl, 1-methylethylaminocarbonyl and 1,1-dimethylethylaminocarbonyl, di-($C_3$-$C_3$)-alkylaminocarbonyl such as dimethylaminocarbonyl, diethylaminocarbonyl, dipropylaminocarbonyl, di-(1-methylethyl)aminocarbonyl, especially dimethylaminocarbonyl and methylethylaminocarbonyl, cyclopropylaminocarbonyl, methylsulfonyl, trifluoromethylsulfonyl;

phenoxy or phenylthio, which can be substituted one to three times by $C_1$-$C_4$-alkyl such as methyl, ethyl, propyl, 1-methylethyl, butyl, 1-methylpropyl, 2-methylpropyl, 1,1-dimethylethyl, especially methyl, $C_1$-$C_4$-haloalkyl such as difluoromethyl, trifluoromethyl, chlorodifluoromethyl, dichlorofluoromethyl, 1-fluoroethyl, 2-fluoroethyl, 2,2-difluoroethyl, 1,1,2,2-tetrafluoroethyl, 2,2,2-trifluoroethyl, 2-chloro-1,1,2-trifluoroethyl and pentafluoroethyl, especially trifluoromethyl, $C_1$-$C_4$-alkoxy such as methoxy, ethoxy, propoxy, 1-methylethoxy, butoxy, 1-methylpropoxy, 2-methylpropoxy and 1,1-dimethylethoxy, especially methoxy, ethoxy, 1-methylethoxy and 1,1-dimethylethoxy, $C_1$-$C_4$-haloalkoxy as mentioned above, especially trifluoromethoxy, $C_1$-$C_4$-alkylthio as mentioned above, especially methylthio, $C_1$-$C_4$-haloalkylthio as mentioned above, especially trifluoromethylthio, halogen, cyano or nitro;

$R^2$ is formyl; fluoro-, chloro- or bromoformyl, 4,5-dihydro-2-oxazolyl;

$COYR^5$ or $CONR^6R^7$ where $R^5$ is hydrogen;

$C_1$-$C_6$-alkyl, preferably $C_1$-$C_4$-alkyl such as methyl, ethyl, 1-methylethyl, 1,1-dimethylethyl, which can carry one to five halogen atoms such as fluorine, chlorine, bromine or iodine, especially fluorine and chlorine, and/or up to three hydroxyl and/or $C_1$-$C_4$-alkoxy groups such as methoxy, ethoxy, n-propoxy, 1-methylethoxy, n-butoxy and 1,1-dimethylethoxy, and/or one of the following:

cyano, $C_1$-$C_4$-alkoxy-$C_2$-$C_4$-alkoxy, especially methoxyethoxy, ethoxyethoxy and propoxyethoxy, $C_1$-$C_3$-alkylthio, especially methylthio and ethylthio, $C_1$-$C_3$-alkylamino such as methylamino, ethylamino and 1-methylethylamino, di-($C_1$-$C_3$)-alkylamino such as dimethylamino, diethylamino, dipropylamino, di-(1-methylethyl)amino and methylethylamino, $C_3$-$C_6$-cycloalkylamino or di-($C_3$-$C_6$)-cycloalkylamino such as cyclopropylamino or dicyclopropylamino, trimethylsilyl, $C_1$-$C_3$-alkylsulfinyl such as methylsulfinyl, 1-methylethylsulfinyl and n-propylsulfinyl, especially methylsulfinyl, $C_1$-$C_3$-alkylsulfonyl such as methylsulfonyl, ethylsulfonyl, 1-methylethylsulfonyl, carboxyl, $C_1$-$C_3$-alkoxycarbonyl such as methoxycarbonyl and ethoxycarbonyl, $C_1$-$C_3$-alkoxycarbonyl-$C_1$-$C_3$-alkoxy such as methoxycarbonylethoxy, $C_1$-$C_3$-alkoxycarbonyl-$C_1$-$C_3$-alkoxy-$C_1$-$C_3$-alkoxycarbonyl such as methoxycarbonylethoxymethoxycarbonyl, di-($C_1$-$C_3$)-alkylaminocarbonyl such as dimethylaminocarbonyl, methylethylaminocarbonyl and di-(1-methylethyl)-aminocarbonyl, di-($C_1$-$C_3$)-alkoxyphosphonyl such as dimethoxyphosphonyl and diethoxyphosphonyl, $C_1$-$C_6$-alkaniminoxy such as 2-propaniminoxy or $C_5$-$C_6$-cycloalkaniminoxy such as cyclopentaniminoxy or cyclohexaniminoxy, N-phthalimido, N-succinimido, benzyloxy or benzoyl, each of which can carry one to three of the following: halogen as mentioned above, especially fluorine and chlorine, $C_1$-$C_3$-alkyl such as methyl, ethyl and 1-methylethyl, especially methyl, ethyl and 1-methylethyl, or $C_1$-$C_3$-alkoxy such as methoxy, ethoxy and 1-methylethoxy, especially methoxy, a 5- or 6-membered saturated heterocyclic radical or a 5- or 6-membered heteroaromatic radical with 1 to 3 hetero atoms in each case, selected from the group comprising oxygen, sulfur and nitrogen, where two oxygen or sulfur atoms or one oxygen atom and one sulfur atom must not be directly adjacent, especially tetrahydrofuran-2-yl-, tetrahydrofuran-3-yl, tetrahydrothien-2-yl, tetrahydrothien-3-yl, tetrahydropyran-2-yl, tetrahydropyran-3-yl, tetrahydropyran-4--yl, pyrrolidin-2-yl, pyrrolidin-3-yl, furan-2-yl, furan-3-yl, thien-2-yl, thien-3-yl, pyrrol-2-yl, pyrrol-3-yl, isoxazol-3-yl, isoxazol-4-yl, isoxazol-5-yl, isothiazo-3-yl, isothiazo-4-yl, isothiazol-5-yl, oxazol-2-yl, oxazol-4-yl, oxazol-5-yl, thiazol-2-yl, thiazol-4-yl, thiazol-5-yl, imidazol-2-yl, imidazol-4-yl, imidazol-5-yl, pyrazol-1-yl, pyrazol-3-yl, pyrazol-4-yl, pyrazol-5-yl, 1,2,3-triazol-1-yl, 1,2,3-triazol-4-yl, 1,2,3-triazol-5-yl, 1,2,4-triazol-1-yl, 1,2,4-triazol-3-yl, 1,2,4-triazol-5-yl, 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl, 1,2,5-thiadiazol-4-yl, 1,3,4-thiadiazol-2-yl, 1,3,4-thiadiazol-5-yl, 1,2,3-oxadiazol-3-yl, 1,2,3-oxadiazol-5-yl, 1,2,4-oxadiazol-3-yl, 1,2,4-oxadiazol-5-yl, 1,2,5-oxadiazol-3-yl, 1,2,5-oxadiazol-4-yl, 1,3,4-oxadiazol-2-yl, 1,3,4-oxadiazol-5-yl, pyrid-2-yl, pyrid-3-yl, pyrid-4-yl, pyrimid-2-yl, pyrimid-4-yl and pyrimid-5-yl, where the heterocycles can also carry one or two of the following substituents: halogen such as fluorine, chlorine, bromine and iodine, especially chlorine and bromine, $C_1$-$C_3$-alkyl such as methyl, ethyl, n-propyl and 1-methylethyl, $C_1$-$C_3$-alkoxy such as methoxy, ethoxy, n-propoxy and 1-methylethoxy and/or $C_1$-$C_3$-alkoxycarbonyl such as methoxycarbonyl, ethoxycarbonyl and 1-methylethoxycarbonyl, phenyl which can carry from one to three of the following substituents: halogen such as fluorine, chlorine, bromine and iodine, especially fluorine and chlorine, nitro, cyano, $C_1$-$C_3$-alkyl such as methyl, ethyl or 1-methylethyl, partially or completely halogenated $C_1$–$C_3$-alkyl such as trifluoromethyl, 1,1,2,2-tetrafluoroethyl and trichloromethyl, $C_1$–$C_3$-alkoxy such as methoxy and 1-methylethoxy and/or partially or completely halogenated $C_1$–$C_3$-alkoxy, especially trifluoromethoxy or $C_1$–$C_2$-alkoxycarbonyl, especially methoxycarbonyl;

—$CR^{10}$=N—$R^{11}$ where $R^{10}$ is hydrogen or branched or unbranched $C_1$–$C_6$-alkyl, especially $C_1$–$C_4$-alkyl such as methyl, ethyl, n-propyl, 1-methylethyl, n-butyl and 1,1-dimethylethyl, $R^{11}$ is $C_1$–$C_6$-alkoxy, $C_3$–$C_6$-alkenyloxy or $C_3$–$C_6$-alkynyloxy, especially $C_1$–$C_4$-alkoxy such as methoxy, ethoxy, n-propoxy, 1-methylethoxy, n-butoxy and 1,1-dimethylethoxy and 2-propenyloxy, 2-butenloxy, 2-propynyloxy and 2-butynyloxy, it being possible for these substituents also to carry from one to three halogen atoms such as fluorine, chlorine, bromine and iodine, especially fluorine and chlorine, and/or a phenyl radical which is unsubstituted or substituted once to three times by halogen as mentioned above, nitro, cyano, $C_1$–$C_3$-alkyl such as methyl, ethyl and n-propyl and/or $C_1$–$C_3$-alkoxy such as methoxy, ethoxy, n-propoxy and 1-methylethoxy;

phenoxy which can also carry from one to three of the following substituents: nitro, cyano, halogen as mentioned above, $C_1$–$C_3$-alkyl as mentioned above and/or $C_4$–$C_3$-alkoxy as mentioned above; branched or unbranched $C_1$–$C_6$-alkylamino, especially methylamino, ethylamino, di-($C_1$–$C_6$)-alkylamino, especially dimethylamino, methylethylamino or phenylamino, the latter also possibly being substituted once to three times by nitro, cyano, halogen as mentioned above, $C_1$–$C_3$-alkyl as mentioned above and/or $C_1$–$C_3$-alkoxy as mentioned above;

$R^5$ is also $C_3$–$C_8$-cycloalkyl, preferably $C_3$–$C_6$-cycloalkyl such as cyclopropyl, cyclopentyl and cyclohexyl;

$C_3$–$C_6$-alkenyl, preferably $C_3$–$C_4$-alkenyl such as 2-propenyl and 2-butenyl, $C_5$–$C_6$-cycloalkenyl such as 2-cyclopentenyl and 2-cyclohexenyl, $C_3$–$C_6$-alkynyl, preferably $C_3$–$C_4$-alkynyl such as 2-propynyl, 2-butynyl and 3-butynyl, it being possible for the last 3 groups to carry one of the following: hydroxyl, halogen such as fluorine, chlorine, bromine and iodine, $C_1$–$C_4$-alkoxy such as methoxy and 1,1-dimethylethoxy or phenyl which in turn can carry one to three of the following: halogen such as fluorine, chlorine or bromine, nitro, cyano, $C_1$–$C_4$-alkyl such as methyl or ethyl, $C_1$–$C_4$-haloalkyl such as fluoromethyl, trifluoromethyl, chlorodifluoromethyl, pentafluoroethyl and 2-chloro TM 1,1,2-trifluoroethyl or $C_1$–$C_4$-alkoxy such as methoxy, 1-methylethoxy, 1,1-dimethylethoxy;

phenyl which can carry from one to three of the following:
halogen such as fluorine, chlorine, bromine and iodine, especially fluorine and chlorine, nitro, cyano, $C_1$–$C_4$-alkyl such as methyl, ethyl and 1,1-dimethylethyl, partially or completely halogenated $C_1$–$C_4$-alkyl such as trifluoromethyl, 1,1,2,2-tetrafluroethyl and trichloromethyl, $C_1$–$C_4$-alkoxy such as methoxy, ethoxy and 1-methylethoxy, partially or completely halogenated $C_1$–$C_4$-alkoxy such as trifluoromethoxy, chlorodifluoromethoxy, 1-fluoroethoxy, pentafluoroethoxy and 2-chloro-1,1,2-trifluoroethoxy or $C_1$–$C_4$-alkoxycarbonyl such as methoxycarbonyl, n-propoxycarbonyl and 1,1-dimethylethoxycarbonyl, a 5- or 6-membered saturated heterocyclic radical or a 5- or 6-membered heteroaromatic radical with 1 to 3 hetero atoms in each case, selected from the group comprising oxygen, sulfur and nitrogen, where two oxygen or sulfur atoms or one oxygen and one sulfur atom must not be directly adjacent, as mentioned above, especially 2-tetrahydrofuranyl, 3-tetrahydrothienyl, 4-tetrahydropyranyl, 2-furanyl, 2-thienyl, 4-isoxazolyl, 5-isothiazolyl, 2-oxazolyl, 4-thiazolyl, 2-imidazolyl, 2-pyrrolyl, 3-pyrazolyl and 4-pyridyl, it being possible for the heterocycles to carry one or two of the following substituents: halogen as mentioned above, $C_1$–$C_3$-alkyl as mentioned above, $C_1$–$C_3$-alkoxy as mentioned above and/or $C_1$–$C_3$-alkoxycarbonyl as mentioned above;

benzotriazolyl;

N-phthalimido, tetrahydrophthalimido, N-succinimido or maleimido;

2,2-dimethyl-1,3-dioxolan-4-ylmethyl or 1,3-dioxolan-2-on-4-ylmethyl;

where Y=O; one equivalent of a cation from the group comprising alkali metals and alkaline earth metals such as sodium, potassium and calcium, manganese, copper, iron, ammonium and ammonium substituted by up to 4 $C_1$–$C_3$-alkyl groups, such as tetramethylammonium;

—N=$CR^6R^9$ where $R^8$ and $R^9$ are each hydrogen, $C_1$–$C_4$-alkyl or partially or completely halogenated $C_1$–$C_4$-alkyl such as methyl, ethyl, 1-methylethyl, tert-butyl, chloromethyl, fluoromethyl, trifluoromethyl, trichloromethyl and 1,1,2,2-tetrafluoroethyl, it being possible for the alkyl or haloalkyl group to carry one of the following radicals:
$C_1$–$C_3$-alkoxy as mentioned above, especially methoxy,
phenyl which can additionally be substituted one to three times by nitro, cyano, halogen as mentioned above, especially fluorine and chlorine, $C_1$–$C_3$-alkyl as mentioned above, especially methyl, ethyl and 1-methylethyl, partially or completely halogenated $C_1$–$C_3$-alkyl as mentioned above, especially trifluoromethyl, $C_1$–$C_3$-alkoxy as mentioned above, especially methoxy and/or partially or completely halogenated $C_1$–$C_3$-alkoxy as mentioned above, especially trifluoromethoxy;

$C_3$–$C_6$-cycloalkyl such as cyclopropyl, cyclopentyl and cyclohexyl;

$C_1$–$C_4$-alkoxy as mentioned above, especially methoxy and ethoxy;

furanyl or phenyl, which can additionally be substituted once to three times by nitro, cyano, halogen as mentioned above, especially fluorine and chlorine, $C_1$–$C_3$-alkyl as mentioned above, especially methyl, ethyl and 1-methylethyl, partially or completely halogenated $C_1$–$C_3$-alkyl as mentioned above, especially trifluoromethyl, $C_1$–$C_3$-alkoxy as mentioned above, especially methoxy and/or partially or completely halogenated $C_1$–$C_3$-alkoxy as mentioned above, especially trifluoromethoxy;

$R^8$ and $R^9$ together are a methylene chain with 4–7, preferably 4–5, members;

or $R^5$ is —W—Z where

W is an ethylene, n-propylene or n-butylene chain, and an ethoxyethylene, 2-butenylene or 2-butynylene chain, and Z is a moiety which is bonded in the ω-position to W and is the same moiety which is linked to W in the α-position of W, for example

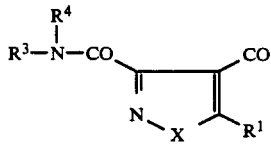 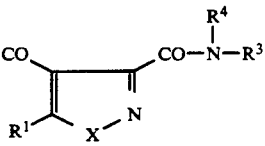

$R^6$ is hydrogen;

$C_1$-$C_6$-alkyl, preferably $C_1$-$C_4$-alkyl such as methyl, ethyl, 1-methylethyl and 1,1-dimethylethyl;

$C_3$-$C_6$-cycloalkyl, preferably $C_3$-$C_6$-cycloalkyl such as cyclopropyl, cyclopentyl and cyclohexyl;

$R^7$ is hydrogen;

$C_1$-$C_6$-alkyl, preferably $C_1$-$C_4$-alkyl such as methyl, ethyl, 1-methylethyl and 1,1-dimethylethyl;

—C($OR^{12}$)=N—H or —C($OR^{12}$)=N—($C_1$-$C_4$)-alkyl where $C_1$-$C_4$-alkyl is alkyl as mentioned above, especially methyl, ethyl and 1-methylethyl, and $R^{12}$ is likewise $C_1$-$C_4$-alkyl as mentioned above, especially methyl;

$R^6$ and $R^7$ together are a methylene chain with 4 to 5 members;

$R^3$ is hydrogen;

$C_1$-$C_6$-alkyl, preferably $C_1$-$C_4$-alkyl such as methyl, ethyl, 1-methylethyl and 1,1-dimethylethyl, which can carry one to three of the following substituents: hydroxyl, halogen, $C_1$-$C_4$-alkoxy such as methoxy and 1,1-dimethylethoxy, $C_1$-$C_4$-alkylthio such as methylthio and 1,1-dimethylethylthio or di-($C_1$-$C_4$)-alkylamino, preferably di-($C_1$-$C_2$)-alkylamino such as dimethylamino and diethylamino;

$C_3$-$C_8$-cycloalkyl, preferably $C_3$-$C_6$-cycloalkyl, such as cyclopropyl, cyclopentyl and cyclohexyl, which can be substituted one to three times by halogen such as fluorine, chlorine and bromine, $C_1$-$C_4$-alkyl such as methyl and 1,1-dimethylethyl or partially or completely halogenated $C_1$-$C_4$-alkyl such as fluoromethyl, trifluoromethyl, chlorodifluoromethyl, pentafluoroethyl and 2-chloro-1,1,2-trifluoroethyl;

$R^4$ is hydrogen, hydroxyl;

$C_1$-$C_4$-alkoxy such as methoxy, ethoxy, 1-methylethoxy, 1,1-dimethylethoxy;

branched or unbranched $C_1$-$C_8$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, especially methyl, ethyl, propyl, 1-methylethyl and 1,1-dimethylethyl, which can carry from one to three of the following radicals: halogen such as fluorine, chlorine and bromine, cyano, $C_1$-$C_4$-alkoxy such as methoxy, ethoxy and 1,1-dimethylethoxy, partially or completely halogenated $C_1$-$C_4$-alkoxy such as fluoromethoxy, trichloromethoxy, 2-chloro-1,1,2-trifluoroethoxy and pentafluoroethoxy, $C_1$-$C_4$-alkylthio such as methylthio, ethylthio and 1,1-dimethylethylthio, $C_1$-$C_4$-haloalkylthio such as fluoromethylthio, trichloromethylthio, 2-chloro-1,1,2-trifluoroethylthio and pentafluoroethylthio, di-($C_1$-$C_4$)-alkylamino, especially di-($C_1$-$C_2$)-alkylamino such as dimethylamino and diethylamino, $C_3$-$C_8$-cycloalkyl, especially $C_3$-$C_6$-cycloalkyl such as cyclopropyl, cyclopentyl and cyclohexyl, or phenyl which can in turn carry up to three of the following groups: halogen such as fluorine, chlorine and bromine, cyano, nitro, $C_1$-$C_4$-alkyl such as methyl, ethyl and 1,1-dimethylethyl, $C_1$-$C_4$-haloalkyl such as fluoromethyl, trichloromethyl, 2-chloro-1,1,2-trifluoroethyl and pentafluoroethyl, $C_1$-$C_4$-alkoxy such as methoxy and 1,1-dimethylethoxy, partially or completely halogenated $C_1$-$C_4$-alkylthio such as fluoromethoxy, trichloromethoxy, 2-chloro-1,1,2-trifluoroethoxy and pentafluoroethoxy, $C_1$-$C_4$-alkylthio such as methylthio and 1,1-dimethylethylthio or $C_1$-$C_4$-haloalkylthio such as fluoromethylthio, trichloromethylthio, 2-chloro-1,1,2-trifluoroethylthio and pentafluoroethylthio;

$C_1$-$C_8$-cycloalkyl, preferably $C_3$-$C_6$-cycloalkyl, especially cyclopropyl, cyclopentyl and cyclohexyl, each of which can carry one to three of the following radicals: halogen such as fluorine, chlorine and bromine, nitro, cyano, $C_1$-$C_6$-alkyl, preferably $C_1$-$C_4$-alkyl such as methyl, ethyl and 1,1-diethylethyl, partially or completely halogenated $C_1$-$C_6$-alkyl, preferably $C_1$-$C_4$-haloalkyl such as fluoromethyl, trichloromethyl, 2-chloro-1,1,2-trifluoroethyl and pentafluoroethyl, $C_1$-$C_4$-alkoxy such as methoxy, 1,1-dimethylethoxy or partially or completely halogenated $C_1$-$C_4$-alkoxy such as fluoromethoxy, trichloromethoxy, 2-chloro-1,1,2-trifluoroethoxy and pentafluoroethoxy;

$C_3$-$C_6$-alkenyl in which the double bond can be epoxidized, or $C_3$-$C_6$-alkynyl, preferably $C_3$-$C_6$-alkenyl or $C_3$-$C_4$-alkynyl, such as 2-propenyl, 2-butenyl, 1,1-dimethyl-2-propenyl, 2-propynyl, 1,1-dimethyl-2-propynyl and 3-butynyl, each of which can be substituted up to three times by halogen such as fluorine, chlorine or bromine and/or once by phenyl which can in turn carry from one to three of the following substituents: halogen, especially fluorine and chlorine, cyano, nitro, $C_1$-$C_4$-alkyl such as methyl and 1,1-dimethylethoxy, partially or completely halogenated $C_1$-$C_4$-alkyl such as fluoromethyl, trifluoromethyl, trichloromethyl, 2-chloro-1,1,2-trifluoroethyl and pentafluoroethyl, $C_1$-$C_4$-alkoxy such as methoxy and 1,1-dimethylethoxy, $C_1$-$C_4$-haloalkoxy such as fluoromethoxy, trifluoromethoxy, trichloromethoxy, 2-chloro-1,1,2-trifluoroethoxy and pentafluoroethoxy, $C_1$-$C_4$-alkylthio such as methylthio and 1,1-dimethylethylthio, partially or completely halogenated $C_1$-$C_4$-alkylthio such as fluoromethylthio, trifluoromethylthio, trichloromethylthio, 2-chloro-1,1,2-trifluoroethylthio and pentafluoroethylthio;

di-($C_1$-$C_4$)-alkylamino, preferably di-($C_1$-$C_2$)-alkylamino such as dimethylamino and diethylamino;

a 5- to 6-membered saturated or aromatic heterocyclic radical containing one or two hetero atoms selected from the group comprising oxygen, sulfur and nitrogen, such as 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 3-pyridyl and 4-pyridyl, which can carry from one to three of the following substituents: $C_1$–$C_4$-alkyl as mentioned above, especially methyl, or halogen as mentioned above, especially fluorine and chlorine;

phenyl which can carry from one to four of the following groups: $C_1$–$C_4$-alkyl as mentioned above, especially methyl, ethyl and 1-methylethyl; partially or completely halogenated $C_1$–$C_4$-alkyl as mentioned above, especially trifluoromethyl and chlorodifluoromethyl; $C_1$–$C_4$-alkoxy as mentioned above, especially methoxy and ethoxy; partially or completely halogenated $C_1$–$C_4$-alkoxy as mentioned above, especially trifluoromethoxy, trichloromethoxy and pentafluoroethoxy; $C_1$–$C_4$-alkylthio as mentioned above, especially methylthio and ethylthio; partially or completely halogenated $C_1$–$C_4$-alkylthio as mentioned above, especially difluoromethylthio, trifluoromethylthio and pentafluoromethylthio, halogen as mentioned above, especially fluorine and chlorine, cyano, nitro, formyl, $C_2$–$C_4$-alkanoyl such as ethanoyl, propanoyl and 1-methylethanoyl, especially ethanoyl, partially or completely halogenated $C_2$–$C_4$-alkanoyl such as trifluoroethanoyl, trichloroethanoyl, pentafluoropropanoyl, especially trifluoroethanoyl or $C_1$–$C_4$-alkoxycarbonyl such as methoxycarbonyl and ethoxycarbonyl;

naphthyl which can be substituted once to three times by $C_1$–$C_4$-alkyl as mentioned above, especially methyl and ethyl, or halogen such as fluorine and chlorine;

$R^3$ and $R^4$ together are a $C_4$–$C_7$-methylene chain which can be interrupted by oxygen, sulfur or N-methyl, such as —(CH$_2$)$_3$—, —(CH$_2$)$_4$—, —(CH$_2$)$_5$—, —(CH$_2$)$_6$—, —CH$_2$—O—CH$_2$—, —CH$_2$—CH$_2$—O—CH$_2$—CH$_2$—, —CH$_2$—S—CH$_2$—, —CH$_2$—CH$_2$—S—CH$_2$—CH$_2$—, —CH$_2$—CH$_2$—N(CH$_3$)—CH$_2$—CH$_2$—, especially —(CH$_2$)$_5$— and —CH$_2$—CH$_2$—O—CH$_2$—CH$_2$—;

or —(CH$_2$)$_3$—CO—.

Compounds I which are particularly preferred with regard to their intended use are listed in the following tables:

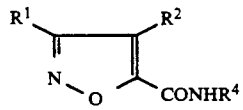

| $R^1$ | $R^2$ | $R^4$ |
|---|---|---|
| Cl | COOH | 1,1-Dimethylethyl |
| Br | COOH | 1,1-Dimethylethyl |
| Methylthio | COOH | 1,1-Dimethylethyl |
| Ethylthio | COOH | 1,1-Dimethylethyl |
| 1-Methylethylthio | COOH | 1,1-Dimethylethyl |
| 1,1-Dimethylethylthio | COOH | 1,1-Dimethylethyl |
| Trifluoromethoxy | COOH | 1,1-Dimethylethyl |
| Trifluoromethylthio | COOH | 1,1-Dimethylethyl |
| Cyano | COOH | 1,1-Dimethylethyl |
| Formyl | COOH | 1,1-Dimethylethyl |
| Acetyl | COOH | 1,1-Dimethylethyl |
| Methoxycarbonyl | COOH | 1,1-Dimethylethyl |
| Ethoxycarbonyl | COOH | 1,1-Dimethylethyl |
| Methylaminocarbonyl | COOH | 1,1-Dimethylethyl |
| Ethylaminocarbonyl | COOH | 1,1-Dimethylethyl |
| 1,1-Dimethylaminocarbonyl | COOH | 1,1-Dimethylethyl |
| Cyclopropylaminocarbonyl | COOH | 1,1-Dimethylethyl |
| Methylsulfonyl | COOH | 1,1-Dimethylethyl |
| Trimethylfluorosulfonyl | COOH | 1,1-Dimethylethyl |
| Phenoxy | COOH | 1,1-Dimethylethyl |
| 2,4-Dichlorophenoxy | COOH | 1,1-Dimethylethyl |
| Phenylthio | COOH | 1,1-Dimethylethyl |
| Cl | COOH | Cyclopropyl |
| Br | COOH | Cyclopropyl |
| Methylthio | COOH | Cyclopropyl |
| Ethylthio | COOH | Cyclopropyl |
| 1-Methylethylthio | COOH | Cyclopropyl |
| 1,1-Dimethylethylthio | COOH | Cyclopropyl |
| Trifluoromethoxy | COOH | Cyclopropyl |
| Trifluoromethylthio | COOH | Cyclopropyl |
| Cyano | COOH | Cyclopropyl |
| Formyl | COOH | Cyclopropyl |
| Acetyl | COOH | Cyclopropyl |
| Methoxycarbonyl | COOH | Cyclopropyl |
| Ethoxycarbonyl | COOH | Cyclopropyl |
| Methylaminocarbonyl | COOH | Cyclopropyl |
| Ethylaminocarbonyl | COOH | Cyclopropyl |
| 1,1-Dimethylaminocarbonyl | COOH | Cyclopropyl |
| Cyclopropylaminocarbonyl | COOH | Cyclopropyl |
| Methylsulfonyl | COOH | Cyclopropyl |
| Trimethylfluorosulfonyl | COOH | Cyclopropyl |

-continued

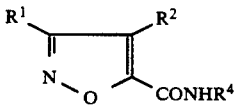

| R¹ | R² | R⁴ |
|---|---|---|
| Phenoxy | COOH | Cyclopropyl |
| 2,4-Dichlorophenoxy | COOH | Cyclopropyl |
| Phenylthio | COOH | Cyclopropyl |
| Cl | COOH | 1,1-Dimethyl-2-propynyl |
| Br | COOH | 1,1-Dimethyl-2-propynyl |
| Methylthio | COOH | 1,1-Dimethyl-2-propynyl |
| Ethylthio | COOH | 1,1-Dimethyl-2-propynyl |
| 1-Methylethylthio | COOH | 1,1-Dimethyl-2-propynyl |
| 1,1-Dimethylethylthio | COOH | 1,1-Dimethyl-2-propynyl |
| Trifluoromethoxy | COOH | 1,1-Dimethyl-2-propynyl |
| Trifluoromethylthio | COOH | 1,1-Dimethyl-2-propynyl |
| Cyano | COOH | 1,1-Dimethyl-2-propynyl |
| Formyl | COOH | 1,1-Dimethyl-2-propynyl |
| Acetyl | COOH | 1,1-Dimethyl-2-propynyl |
| Methoxycarbonyl | COOH | 1,1-Dimethyl-2-propynyl |
| Ethoxycarbonyl | COOH | 1,1-Dimethyl-2-propynyl |
| Methylaminocarbonyl | COOH | 1,1-Dimethyl-2-propynyl |
| Ethylaminocarbonyl | COOH | 1,1-Dimethyl-2-propynyl |
| 1,1-Dimethylaminocarbonyl | COOH | 1,1-Dimethyl-2-propynyl |
| Cyclopropylaminocarbonyl | COOH | 1,1-Dimethyl-2-propynyl |
| Methylsulfonyl | COOH | 1,1-Dimethyl-2-propynyl |
| Trimethylfluorosulfonyl | COOH | 1,1-Dimethyl-2-propynyl |
| Phenoxy | COOH | 1,1-Dimethyl-2-propynyl |
| 2,4-Dichlorophenoxy | COOH | 1,1-Dimethyl-2-propynyl |
| Phenylthio | COOH | 1,1-Dimethyl-2-propynyl |
| Cl | COOH | 1-Methylcyclopropyl |
| Br | COOH | 1-Methylcyclopropyl |
| Methylthio | COOH | 1-Methylcyclopropyl |
| Ethylthio | COOH | 1-Methylcyclopropyl |
| 1-Methylethylthio | COOH | 1-Methylcyclopropyl |
| 1,1-Dimethylethylthio | COOH | 1-Methylcyclopropyl |
| Trifluoromethoxy | COOH | 1-Methylcyclopropyl |
| Trifluoromethylthio | COOH | 1-Methylcyclopropyl |
| Cyano | COOH | 1-Methylcyclopropyl |
| Formyl | COOH | 1-Methylcyclopropyl |
| Acetyl | COOH | 1-Methylcyclopropyl |
| Methoxycarbonyl | COOH | 1-Methylcyclopropyl |
| Ethoxycarbonyl | COOH | 1-Methylcyclopropyl |
| Methylaminocarbonyl | COOH | 1-Methylcyclopropyl |
| Ethylaminocarbonyl | COOH | 1-Methylcyclopropyl |
| 1,1-Dimethylaminocarbonyl | COOH | 1-Methylcyclopropyl |
| Cyclopropylaminocarbonyl | COOH | 1-Methylcyclopropyl |
| Methylsulfonyl | COOH | 1-Methylcyclopropyl |
| Trimethylfluorosulfonyl | COOH | 1-Methylcyclopropyl |
| Phenoxy | COOH | 1-Methylcyclopropyl |
| 2,4-Dichlorophenoxy | COOH | 1-Methylcyclopropyl |
| Phenylthio | COOH | 1-Methylcyclopropyl |
| Cl | COOH | 1-Cyclopropylethyl |
| Br | COOH | 1-Cyclopropylethyl |
| Methylthio | COOH | 1-Cyclopropylethyl |
| Ethylthio | COOH | 1-Cyclopropylethyl |
| 1-Methylethylthio | COOH | 1-Cyclopropylethyl |
| 1,1-Dimethylethylthio | COOH | 1-Cyclopropylethyl |
| Trifluoromethoxy | COOH | 1-Cyclopropylethyl |
| Trifluoromethylthio | COOH | 1-Cyclopropylethyl |
| Cyano | COOH | 1-Cyclopropylethyl |
| Formyl | COOH | 1-Cyclopropylethyl |
| Acetyl | COOH | 1-Cyclopropylethyl |
| Methoxycarbonyl | COOH | 1-Cyclopropylethyl |
| Ethoxycarbonyl | COOH | 1-Cyclopropylethyl |
| Methylaminocarbonyl | COOH | 1-Cyclopropylethyl |
| Ethylaminocarbonyl | COOH | 1-Cyclopropylethyl |
| 1,1-Dimethylaminocarbonyl | COOH | 1-Cyclopropylethyl |
| Cyclopropylaminocarbonyl | COOH | 1-Cyclopropylethyl |
| Methylsulfonyl | COOH | 1-Cyclopropylethyl |
| Trimethylfluorosulfonyl | COOH | 1-Cyclopropylethyl |
| Phenoxy | COOH | 1-Cyclopropylethyl |
| 2,4-Dichlorophenoxy | COOH | 1-Cyclopropylethyl |
| Phenylthio | COOH | 1-Cyclopropylethyl |
| Cl | COOH | 1,1-Dimethyl-2-propenyl |
| Br | COOH | 1,1-Dimethyl-2-propenyl |
| Methylthio | COOH | 1,1-Dimethyl-2-propenyl |
| Ethylthio | COOH | 1,1-Dimethyl-2-propenyl |
| 1-Methylethylthio | COOH | 1,1-Dimethyl-2-propenyl |
| 1,1-Dimethylethylthio | COOH | 1,1-Dimethyl-2-propenyl |

-continued

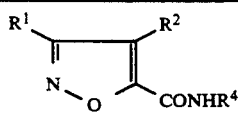

| R¹ | R² | R⁴ |
|---|---|---|
| Trifluoromethoxy | COOH | 1,1-Dimethyl-2-propenyl |
| Trifluoromethylthio | COOH | 1,1-Dimethyl-2-propenyl |
| Cyano | COOH | 1,1-Dimethyl-2-propenyl |
| Formyl | COOH | 1,1-Dimethyl-2-propenyl |
| Acetyl | COOH | 1,1-Dimethyl-2-propenyl |
| Methoxycarbonyl | COOH | 1,1-Dimethyl-2-propenyl |
| Ethoxycarbonyl | COOH | 1,1-Dimethyl-2-propenyl |
| Methylaminocarbonyl | COOH | 1,1-Dimethyl-2-propenyl |
| Ethylaminocarbonyl | COOH | 1,1-Dimethyl-2-propenyl |
| 1,1-Dimethylaminocarbonyl | COOH | 1,1-Dimethyl-2-propenyl |
| Cyclopropylaminocarbonyl | COOH | 1,1-Dimethyl-2-propenyl |
| Methylsulfonyl | COOH | 1,1-Dimethyl-2-propenyl |
| Trimethylfluorosulfonyl | COOH | 1,1-Dimethyl-2-propenyl |
| Phenoxy | COOH | 1,1-Dimethyl-2-propenyl |
| 2,4-Dichlorophenoxy | COOH | 1,1-Dimethyl-2-propenyl |
| Phenylthio | COOH | 1,1-Dimethyl-2-propenyl |
| Cl | COO—N=C(CH₃)₂ | 1,1-Dimethylethyl |
| Br | COO—N=C(CH₃)₂ | 1,1-Dimethylethyl |
| Methylthio | COO—N=C(CH₃)₂ | 1,1-Dimethylethyl |
| Ethylthio | COO—N=C(CH₃)₂ | 1,1-Dimethylethyl |
| 1-Methylethylthio | COO—N=C(CH₃)₂ | 1,1-Dimethylethyl |
| 1,1-Dimethylethylthio | COO—N=C(CH₃)₂ | 1,1-Dimethylethyl |
| Trifluoromethoxy | COO—N=C(CH₃)₂ | 1,1-Dimethylethyl |
| Trifluoromethylthio | COO—N=C(CH₃)₂ | 1,1-Dimethylethyl |
| Cyano | COO—N=C(CH₃)₂ | 1,1-Dimethylethyl |
| Formyl | COO—N=C(CH₃)₂ | 1,1-Dimethylethyl |
| Acetyl | COO—N=C(CH₃)₂ | 1,1-Dimethylethyl |
| Methoxycarbonyl | COO—N=C(CH₃)₂ | 1,1-Dimethylethyl |
| Ethoxycarbonyl | COO—N=C(CH₃)₂ | 1,1-Dimethylethyl |
| Methylaminocarbonyl | COO—N=C(CH₃)₂ | 1,1-Dimethylethyl |
| Ethylaminocarbonyl | COO—N=C(CH₃)₂ | 1,1-Dimethylethyl |
| 1,1-Dimethylaminocarbonyl | COO—N=C(CH₃)₂ | 1,1-Dimethylethyl |
| Cyclopropylaminocarbonyl | COO—N=C(CH₃)₂ | 1,1-Dimethylethyl |
| Methylsulfonyl | COO—N=C(CH₃)₂ | 1,1-Dimethylethyl |
| Trimethylfluorosulfonyl | COO—N=C(CH₃)₂ | 1,1-Dimethylethyl |
| Phenoxy | COO—N=C(CH₃)₂ | 1,1-Dimethylethyl |
| 2,4-Dichlorophenoxy | COO—N=C(CH₃)₂ | 1,1-Dimethylethyl |
| Phenylthio | COO—N=C(CH₃)₂ | 1,1-Dimethylethyl |
| Cl | COO—N=C(CH₃)₂ | Cyclopropyl |
| Br | COO—N=C(CH₃)₂ | Cyclopropyl |
| Methylthio | COO—N=C(CH₃)₂ | Cyclopropyl |
| Ethylthio | COO—N=C(CH₃)₂ | Cyclopropyl |
| 1-Methylethylthio | COO—N=C(CH₃)₂ | Cyclopropyl |
| 1,1-Dimethylethylthio | COO—N=C(CH₃)₂ | Cyclopropyl |
| Trifluoromethoxy | COO—N=C(CH₃)₂ | Cyclopropyl |
| Trifluoromethylthio | COO—N=C(CH₃)₂ | Cyclopropyl |
| Cyano | COO—N=C(CH₃)₂ | Cyclopropyl |
| Formyl | COO—N=C(CH₃)₂ | Cyclopropyl |
| Acetyl | COO—N=C(CH₃)₂ | Cyclopropyl |
| Methoxycarbonyl | COO—N=C(CH₃)₂ | Cyclopropyl |
| Ethoxycarbonyl | COO—N=C(CH₃)₂ | Cyclopropyl |
| Methylaminocarbonyl | COO—N=C(CH₃)₂ | Cyclopropyl |
| Ethylaminocarbonyl | COO—N=C(CH₃)₂ | Cyclopropyl |
| 1,1-Dimethylaminocarbonyl | COO—N=C(CH₃)₂ | Cyclopropyl |
| Cyclopropylaminocarbonyl | COO—N=C(CH₃)₂ | Cyclopropyl |
| Methylsulfonyl | COO—N=C(CH₃)₂ | Cyclopropyl |
| Trimethylfluorosulfonyl | COO—N=C(CH₃)₂ | Cyclopropyl |
| Phenoxy | COO—N=C(CH₃)₂ | Cyclopropyl |
| 2,4-Dichlorophenoxy | COO—N=C(CH₃)₂ | Cyclopropyl |
| Phenylthio | COO—N=C(CH₃)₂ | Cyclopropyl |
| Cl | COO—N=C(CH₃)₂ | 1,1-Dimethyl-2-propynyl |
| Br | COO—N=C(CH₃)₂ | 1,1-Dimethyl-2-propynyl |
| Methylthio | COO—N=C(CH₃)₂ | 1,1-Dimethyl-2-propynyl |
| Ethylthio | COO—N=C(CH₃)₂ | 1,1-Dimethyl-2-propynyl |
| 1-Methylethylthio | COO—N=C(CH₃)₂ | 1,1-Dimethyl-2-propynyl |
| 1,1-Dimethylethylthio | COO—N=C(CH₃)₂ | 1,1-Dimethyl-2-propynyl |
| Trifluoromethoxy | COO—N=C(CH₃)₂ | 1,1-Dimethyl-2-propynyl |
| Trifluoromethylthio | COO—N=C(CH₃)₂ | 1,1-Dimethyl-2-propynyl |
| Cyano | COO—N=C(CH₃)₂ | 1,1-Dimethyl-2-propynyl |
| Formyl | COO—N=C(CH₃)₂ | 1,1-Dimethyl-2-propynyl |
| Acetyl | COO—N=C(CH₃)₂ | 1,1-Dimethyl-2-propynyl |
| Methoxycarbonyl | COO—N=C(CH₃)₂ | 1,1-Dimethyl-2-propynyl |
| Ethoxycarbonyl | COO—N=C(CH₃)₂ | 1,1-Dimethyl-2-propynyl |
| Methylaminocarbonyl | COO—N=C(CH₃)₂ | 1,1-Dimethyl-2-propynyl |
| Ethylaminocarbonyl | COO—N=C(CH₃)₂ | 1,1-Dimethyl-2-propynyl |

-continued

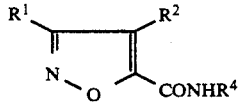

| R¹ | R² | R⁴ |
|---|---|---|
| 1,1-Dimethylaminocarbonyl | COO—N=C(CH₃)₂ | 1,1-Dimethyl-2-propynyl |
| Cyclopropylaminocarbonyl | COO—N=C(CH₃)₂ | 1,1-Dimethyl-2-propynyl |
| Methylsulfonyl | COO—N=C(CH₃)₂ | 1,1-Dimethyl-2-propynyl |
| Trimethylfluorosulfonyl | COO—N=C(CH₃)₂ | 1,1-Dimethyl-2-propynyl |
| Phenoxy | COO—N=C(CH₃)₂ | 1,1-Dimethyl-2-propynyl |
| 2,4-Dichlorophenoxy | COO—N=C(CH₃)₂ | 1,1-Dimethyl-2-propynyl |
| Phenylthio | COO—N=C(CH₃)₂ | 1,1-Dimethyl-2-propynyl |
| Cl | COO—CH₂—CH=NOCH₃ | 1,1-Dimethylethyl |
| Br | COO—CH₂—CH=NOCH₃ | 1,1-Dimethylethyl |
| Methylthio | COO—CH₂—CH=NOCH₃ | 1,1-Dimethylethyl |
| Ethylthio | COO—CH₂—CH=NOCH₃ | 1,1-Dimethylethyl |
| 1-Methylethylthio | COO—CH₂—CH=NOCH₃ | 1,1-Dimethylethyl |
| 1,1-Dimethylethylthio | COO—CH₂—CH=NOCH₃ | 1,1-Dimethylethyl |
| Trifluoromethoxy | COO—CH₂—CH=NOCH₃ | 1,1-Dimethylethyl |
| Trifluoromethylthio | COO—CH₂—CH=NOCH₃ | 1,1-Dimethylethyl |
| Cyano | COO—CH₂—CH=NOCH₃ | 1,1-Dimethylethyl |
| Formyl | COO—CH₂—CH=NOCH₃ | 1,1-Dimethylethyl |
| Acetyl | COO—CH₂—CH=NOCH₃ | 1,1-Dimethylethyl |
| Methoxycarbonyl | COO—CH₂—CH=NOCH₃ | 1,1-Dimethylethyl |
| Ethoxycarbonyl | COO—CH₂—CH=NOCH₃ | 1,1-Dimethylethyl |
| Methylaminocarbonyl | COO—CH₂—CH=NOCH₃ | 1,1-Dimethylethyl |
| Ethylaminocarbonyl | COO—CH₂—CH=NOCH₃ | 1,1-Dimethylethyl |
| 1,1-Dimethylaminocarbonyl | COO—CH₂—CH=NOCH₃ | 1,1-Dimethylethyl |
| Cyclopropylaminocarbonyl | COO—CH₂—CH=NOCH₃ | 1,1-Dimethylethyl |
| Methylsulfonyl | COO—CH₂—CH=NOCH₃ | 1,1-Dimethylethyl |
| Trimethylfluorosulfonyl | COO—CH₂—CH=NOCH₃ | 1,1-Dimethylethyl |
| Phenoxy | COO—CH₂—CH=NOCH₃ | 1,1-Dimethylethyl |
| 2,4-Dichlorophenoxy | COO—CH₂—CH=NOCH₃ | 1,1-Dimethylethyl |
| Phenylthio | COO—CH₂—CH=NOCH₃ | 1,1-Dimethylethyl |
| Cl | COOCH₂—CH=NOC₂H₅ | 1,1-Dimethylethyl |
| Br | COOCH₂—CH=NOC₂H₅ | 1,1-Dimethylethyl |
| Methylthio | COOCH₂—CH=NOC₂H₅ | 1,1-Dimethylethyl |
| Ethylthio | COOCH₂—CH=NOC₂H₅ | 1,1-Dimethylethyl |
| 1-Methylethylthio | COOCH₂—CH=NOC₂H₅ | 1,1-Dimethylethyl |
| 1,1-Dimethylethylthio | COOCH₂—CH=NOC₂H₅ | 1,1-Dimethylethyl |
| Trifluoromethoxy | COOCH₂—CH=NOC₂H₅ | 1,1-Dimethylethyl |
| Trifluoromethylthio | COOCH₂—CH=NOC₂H₅ | 1,1-Dimethylethyl |
| Cyano | COOCH₂—CH=NOC₂H₅ | 1,1-Dimethylethyl |
| Formyl | COOCH₂—CH=NOC₂H₅ | 1,1-Dimethylethyl |
| Acetyl | COOCH₂—CH=NOC₂H₅ | 1,1-Dimethylethyl |
| Methoxycarbonyl | COOCH₂—CH=NOC₂H₅ | 1,1-Dimethylethyl |
| Ethoxycarbonyl | COOCH₂—CH=NOC₂H₅ | 1,1-Dimethylethyl |
| Methylaminocarbonyl | COOCH₂—CH=NOC₂H₅ | 1,1-Dimethylethyl |
| Ethylaminocarbonyl | COOCH₂—CH=NOC₂H₅ | 1,1-Dimethylethyl |
| 1,1-Dimethylaminocarbonyl | COOCH₂—CH=NOC₂H₅ | 1,1-Dimethylethyl |
| Cyclopropylaminocarbonyl | COOCH₂—CH=NOC₂H₅ | 1,1-Dimethylethyl |
| Methylsulfonyl | COOCH₂—CH=NOC₂H₅ | 1,1-Dimethylethyl |
| Trimethylfluorosulfonyl | COOCH₂—CH=NOC₂H₅ | 1,1-Dimethylethyl |
| Phenoxy | COOCH₂—CH=NOC₂H₅ | 1,1-Dimethylethyl |
| 2,4-Dichlorophenoxy | COOCH₂—CH=NOC₂H₅ | 1,1-Dimethylethyl |
| Phenylthio | COOCH₂—CH=NOC₂H₅ | 1,1-Dimethylethyl |
| Cl | COOCH₂—CH=NOCH₃ | 1,1-Dimethyl-2-propynyl |
| Br | COOCH₂—CH=NOCH₃ | 1,1-Dimethyl-2-propynyl |
| Methylthio | COOCH₂—CH=NOCH₃ | 1,1-Dimethyl-2-propynyl |
| Ethylthio | COOCH₂—CH=NOCH₃ | 1,1-Dimethyl-2-propynyl |
| 1-Methylethylthio | COOCH₂—CH=NOCH₃ | 1,1-Dimethyl-2-propynyl |
| 1,1-Dimethylethylthio | COOCH₂—CH=NOCH₃ | 1,1-Dimethyl-2-propynyl |
| Trifluoromethoxy | COOCH₂—CH=NOCH₃ | 1,1-Dimethyl-2-propynyl |
| Trifluoromethylthio | COOCH₂—CH=NOCH₃ | 1,1-Dimethyl-2-propynyl |
| Cyano | COOCH₂—CH=NOCH₃ | 1,1-Dimethyl-2-propynyl |
| Formyl | COOCH₂—CH=NOCH₃ | 1,1-Dimethyl-2-propynyl |
| Acetyl | COOCH₂—CH=NOCH₃ | 1,1-Dimethyl-2-propynyl |
| Methoxycarbonyl | COOCH₂—CH=NOCH₃ | 1,1-Dimethyl-2-propynyl |
| Ethoxycarbonyl | COOCH₂—CH=NOCH₃ | 1,1-Dimethyl-2-propynyl |
| Methylaminocarbonyl | COOCH₂—CH=NOCH₃ | 1,1-Dimethyl-2-propynyl |
| Ethylaminocarbonyl | COOCH₂—CH=NOCH₃ | 1,1-Dimethyl-2-propynyl |
| 1,1-Dimethylaminocarbonyl | COOCH₂—CH=NOCH₃ | 1,1-Dimethyl-2-propynyl |
| Cyclopropylaminocarbonyl | COOCH₂—CH=NOCH₃ | 1,1-Dimethyl-2-propynyl |
| Methylsulfonyl | COOCH₂—CH=NOCH₃ | 1,1-Dimethyl-2-propynyl |
| Trimethylfluorosulfonyl | COOCH₂—CH=NOCH₃ | 1,1-Dimethyl-2-propynyl |
| Phenoxy | COOCH₂—CH=NOCH₃ | 1,1-Dimethyl-2-propynyl |
| 2,4-Dichlorophenoxy | COOCH₂—CH=NOCH₃ | 1,1-Dimethyl-2-propynyl |
| Phenylthio | COOCH₂—CH=NOCH₃ | 1,1-Dimethyl-2-propynyl |
| Cl | COO—CH₂—CH=NOC₂H₅ | 1,1-Dimethyl-2-propynyl |
| Br | COO—CH₂—CH=NOC₂H₅ | 1,1-Dimethyl-2-propynyl |

-continued

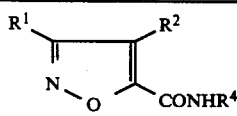

| R¹ | R² | R⁴ |
|---|---|---|
| Methylthio | COO—CH₂—CH=NOC₂H₅ | 1,1-Dimethyl-2-propynyl |
| Ethylthio | COO—CH₂—CH=NOC₂H₅ | 1,1-Dimethyl-2-propynyl |
| 1-Methylethylthio | COO—CH₂—CH=NOC₂H₅ | 1,1-Dimethyl-2-propynyl |
| 1,1-Dimethylethylthio | COO—CH₂—CH=NOC₂H₅ | 1,1-Dimethyl-2-propynyl |
| Trifluoromethoxy | COO—CH₂—CH=NOC₂H₅ | 1,1-Dimethyl-2-propynyl |
| Trifluoromethylthio | COO—CH₂—CH=NOC₂H₅ | 1,1-Dimethyl-2-propynyl |
| Cyano | COO—CH₂—CH=NOC₂H₅ | 1,1-Dimethyl-2-propynyl |
| Formyl | COO—CH₂—CH=NOC₂H₅ | 1,1-Dimethyl-2-propynyl |
| Acetyl | COO—CH₂—CH=NOC₂H₅ | 1,1-Dimethyl-2-propynyl |
| Methoxycarbonyl | COO—CH₂—CH=NOC₂H₅ | 1,1-Dimethyl-2-propynyl |
| Ethoxycarbonyl | COO—CH₂—CH=NOC₂H₅ | 1,1-Dimethyl-2-propynyl |
| Methylaminocarbonyl | COO—CH₂—CH=NOC₂H₅ | 1,1-Dimethyl-2-propynyl |
| Ethylaminocarbonyl | COO—CH₂—CH=NOC₂H₅ | 1,1-Dimethyl-2-propynyl |
| 1,1-Dimethylaminocarbonyl | COO—CH₂—CH=NOC₂H₅ | 1,1-Dimethyl-2-propynyl |
| Cyclopropylaminocarbonyl | COO—CH₂—CH=NOC₂H₅ | 1,1-Dimethyl-2-propynyl |
| Methylsulfonyl | COO—CH₂—CH=NOC₂H₅ | 1,1-Dimethyl-2-propynyl |
| Trimethylfluorosulfonyl | COO—CH₂—CH=NOC₂H₅ | 1,1-Dimethyl-2-propynyl |
| Phenoxy | COO—CH₂—CH=NOC₂H₅ | 1,1-Dimethyl-2-propynyl |
| 2,4-Dichlorophenoxy | COO—CH₂—CH=NOC₂H₅ | 1,1-Dimethyl-2-propynyl |
| Phenylthio | COO—CH₂—CH=NOC₂H₅ | 1,1-Dimethyl-2-propynyl |

Also of particular interest are the halogen-substituted compounds I, eg.

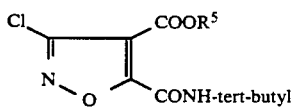

where $R^5$ is hydrogen or the following: methyl, ethyl, propyl, 1-methylethyl, 1,1-dimethylethyl, 2,2-trifluoroethyl, 2-chloroethyl, 2,2,2-trichloroethyl, 2,3-dihydroxypropyl, 2-methoxyethyl, 2,2-dimethoxyethyl, 2,2,2-trimethoxyethyl, 2-methoxyethoxymethyl, 2-methylthioethyl, 2-methylaminoethyl, 2-cyclopropylaminoethyl, 2-dicyclopropylaminoethyl, 2-trimethylsilylethyl, 2-methylsulfinylethyl, 2-methylsulfonylethyl, carboxymethyl, methoxycarbonylmethyl, dimethylaminocarbonylmethyl, diethoxyphosphonylmethyl, CH₂—CH₂—O—N=C(CH₃)₂,

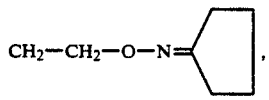

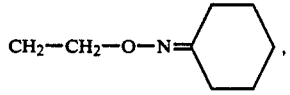

N-phthalimidomethyl, N-succinimidomethyl, benzyloxymethyl, (4-Br-benzoyl)-methyl, (4-methoxybenzoyl)-methyl, 2-tetrahydrofuranylmethyl, 2-tetrahydrothienylmethyl, 4-tetrahydropyranylmethyl, 2-furanylmethyl, 2-thienylmethyl, benzyl, 2,4-dichlorobenzyl, 2-phenylethyl, CH₂—CH=N—OCH₃, CH₂—CH=N—OC₂H₅, CH₂—CH=N—OC₃H₇, CH₂—C(CH₃)=NOCH₃, CH₂—C(CH₃)=NOC₂H₅, CH₂—CH=N—OCH₂CH=CH₂, CH₂—CH=N—OCH₂—C≡CH,

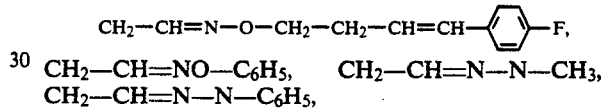

CH₂—CH=NO—C₆H₅, CH₂—CH=N—N—CH₃, CH₂—CH=N—N—C₆H₅,

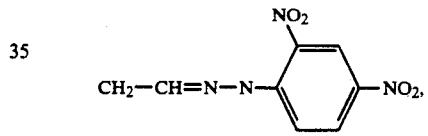

cyclopentyl, cyclohexyl, 2-propenyl, E—CH₂—CH=CH=C₆H₅, 2-propynyl, 3-iodopropargyl, 4-methylphenyl, 4-methoxyphenyl, 4-fluorophenyl, 4-chlorophenyl, 4-bromophenyl, 4-cyanophenyl, 4-nitrophenyl, 2-chlorophenyl, 2,4-dimethoxyphenyl, 2,6-dibromo-4-cyanophenyl, 2-tetrahydrofuranyl, 2-tetrahydropyranyl, 1-pyrazolyl, 1,2,3-triazol-1-yl, 1-benzotriazolyl, phthalimido, succinimido, maleimido, Na+, K+, NH₄+, +NH₃-(1-methylethyl), +NH₂-(1-methylethyl)₂, 2-propanimino, 2-butanimino, —N=C(C₂H₅)₂,

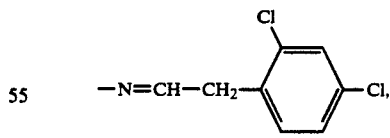

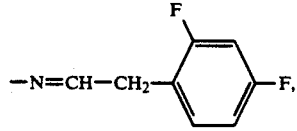

—N=C(cyclopropyl)₂, cyclopentanimino, cyclohexanimino.

The compounds I and the herbicidal agents containing them can be applied, for example in the form of directly sprayable solutions, powders, suspensions, including high-percentage aqueous, oily or other suspensions or dispersions, emulsions, oil dispersions, pastes, dusting or broadcasting agents, or granules, by spraying, atomizing, dusting, broadcasting or watering. The application forms depend on the purposes for which they are used; they ought in every case to ensure the finest possible distribution of the novel active ingredients.

The compounds I are generally suitable for preparing directly sprayable solutions, emulsions, pastes or oil dispersions. Suitable inert additives are mineral oil fractions of medium to high boiling point, such as kerosine or diesel oil, also coaltar oils and oils of vegetable or animal origin, aliphatic, cyclic and aromatic hydrocarbons, eg. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or highly polar solvents such as N,N-dimethylformamide, dimethyl sulfoxide, N-methylpyrrolidone and water.

Aqueous application forms can be prepared from emulsion concentrates, dispersions, pastes, wettable powders or water-dispersible granules by adding water. To prepare emulsions, pastes or oil dispersions, the substances can be homogenized, as such or dissolved in an oil or solvent, using wetting agents, adhesion promoters, dispersants or emulsifiers, in water. However, it is also possible to prepare concentrates which are composed of active substance, wetting agent, adhesion promoter, dispersant or emulsifier and, where appropriate, solvent or oil and which are suitable for dilution with water.

Suitable surfactants are the alkali metal, alkaline earth metal and ammonium salts of aromatic sulfonic acids, such as lignin-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and of fatty alcohol glycol ether, products of the condensation of sulfonated naphthalene and naphthalene derivatives with formaldehyde, products of the condensation of naphthalene or naphthalenesulfonic acids with phenol and formaldehyde, polyoxyethylene octylphenol ether, ethoxylated isooctyl-, octyl- or nonylphenol, alkylphenol and tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignin-sulfite waste liquors and methylcellulose.

Powders and dusting and broadcasting agents can be prepared by mixing or grinding the active substances together with a solid carrier.

Granules, eg. coated, impregnated or homogeneous granules, can be prepared by binding the active ingredients to solid carriers. Examples of solid carriers are mineral earths such as silica gel, silicic acids, silicates, talc, kaolin, limestone, lime, chalk, bole, loess, clay, dolomite, diatomaceous earth, calcium and magnesium sulfates, magnesium oxide, ground plastics, fertilizers such as ammonium sulfate, ammonium phosphate, ammonium nitrate, ureas and vegetable products such as cereals flour, bark meal, wood meal and nutshell meal, cellulose powders or other solid carriers.

The formulations contain from 0.1 to 95% by weight, preferably from 0.5 to 90% by weight, of active ingredient. The active ingredients are employed in a purity of from 90 to 100%, preferably 95 to 100% (according to the NMR spectrum).

The compounds I according to the invention can be formulated as follows, for example:

I. 90 parts by weight of compound 1.001 are mixed with 10 parts by weight of N-methyl-α-pyrrolidone to give a solution which is suitable for use in the form of very small drops.

II. 20 parts by weight of compound 1.009 are dissolved in a mixture of 80 parts by weight of xylene, 10 parts by weight of the adduct of 8 to 10 moles of ethylene oxide and 1 mole of oleic acid N-monoethanolamide, 5 parts by weight of calcium dodecylbenzenesulfonate, 5 parts by weight of the adduct of 40 moles of ethylene oxide and 1 mole of castor oil. A fine dispersion of the solution in 100,000 parts by weight of water contains 0.02% by weight of active ingredient.

III. 20 parts by weight of compound 1.015 are dissolved in a mixture of 40 parts by weight of cyclohexanone, 30 parts by weight of isobutanol, 20 parts by weight of the adduct of 7 moles of ethylene oxide and 1 mole of isooctylphenol and 10 parts by weight of the adduct of 40 moles of ethylene oxide and 1 mole of castor oil. A fine dispersion of the solution in 100,000 parts by weight of water contains 0.02% by weight of active ingredient.

IV. 20 parts by weight of active ingredient 1.07 are dissolved in a mixture of 25 parts by weight of cyclohexanone, 65 parts by weight of a mineral oil fraction of boiling point 210° to 280° C. and 10 parts by weight of the adduct of 40 moles of ethylene oxide and 1 mole of castor oil. A fine dispersion in 100,000 parts by weight of water contains 0.02% by weight of active ingredient.

V. 20 parts by weight of active ingredient 1.005 are thoroughly mixed with 3 parts by weight of sodium diisobutylnaphthalene-α-sulfonate, 17 parts by weight of the sodium salt of a ligninsulfonic acid from a sulfite waste liquor and 60 parts by weight of powdered silica gel and milled in a hammer mill. A fine dispersion of the mixture in 20,000 parts by weight of water contains 0.1% by weight of active ingredient and can be used for spraying.

VI. 3 parts by weight of active ingredient 1.015 are mixed with 97 parts by weight of finely divided kaolin. This results in a dusting agent which contains 3% by weight of active ingredient.

VII. 30 parts by weight of active ingredient 1.009 are intimately mixed with a mixture of 92 parts by weight of powdered silica gel and 8 parts by weight of liquid paraffin which has been sprayed onto the surface of the silica gel. This results in a formulation of the active ingredient with good adhesion.

VIII. 20 parts by weight of active ingredient 1.001 are intimately mixed with 2 parts by weight of calcium dodecylbenzenesulfonate, 8 parts by weight of fatty alcohol polyglycol ether, 2 parts by weight of a sodium salt of a phenol/urea/formaldehyde condensate and 68 parts by weight of a liquid paraffin. A stable oily dispersion is obtained.

The herbicidal agents or the active ingredients can be applied by a pre-emergence or post-emergence method. If the active ingredients are less well tolerated by certain crops, the application techniques can be such that the herbicidal agents are sprayed so as to avoid as far as possible the leaves of the sensitive crops, while the active ingredients reach the leaves of unwanted plants growing underneath them or the uncovered surface of the soil (post-directed, lay-by).

The application rates of herbicidal active ingredient depend on the aim of the control, the season, the target plants and the stage of growth and range from 0.001 to 3.0, preferably 0.01 to 2.0, kg/ha active substance.

In view of the wide variety of application methods, the novel compounds and the agents containing them can also be employed to eradicate unwanted plants in a number of other crops. Examples of suitable crops are the following:

| Botanical name | English name |
|---|---|
| Allium cepa | cooking onion |
| Ananas comosus | pineapple |
| Arachis hypogaea | peanut |
| Asparagus officinalis | asparagus |
| Beta vulgaris spp. altissima | sugar beet |
| Beta vulgaris spp. rapa | fodder beet |
| Brassica napus var. napus | rape |
| Brassica napus var. napobrassica | Swedish turnip |
| Camellia sinensis | tea plant |
| Carthamus tinctorius | safflower |
| Carya illinoinensis | pecan nut |
| Citrus limon | lemon |
| Citrus sinensis | orange |
| Coffea arabica (Coffea canephora, Coffea liberica) | coffee |
| Cucumis sativus | cucumber |
| Cynodon dactylon | Bermuda grass |
| Daucus carota | carrot |
| Elaeis guineensis | oil palm |
| Fragaria vesca | strawberry |
| Glycine max | soybean |
| Gossypium hirsutum (Gossypium arboreum, Gossypium herbaceum, Gossypium vitifolium) | cotton |
| Helianthus annuus | sunflower |
| Hevea brasiliensis | para rubber tree |
| Hordeum vulgare | barley |
| Humulus lupulus | hops |
| Ipomoea batatas | sweet potatoes |
| Juglans regia | walnut |
| Lens culinaris | lentil |
| Linum usitatissimum | flax |
| Lycopersicon lycopersicum | tomato |
| Malus spp. | apple |
| Manihot esculenta | cassava |
| Medicago sativa | alfalfa |
| Musa spp. | bananas |
| Nicotiana tabacum (N. rustica) | tobacco |
| Olea europaea | olive |
| Oryza sativa | rice |
| Phaseolus lunatus | lima bean |
| Phaseolus vulgaris | bush bean |
| Picea abies | spruce |
| Pinus spp. | pine |
| Pisum sativum | garden pea |
| Prunus avium | sweet cherry |
| Prunus persica | peach |
| Pyrus communis | pear |
| Ribes sylvestre | redcurrant |
| Ricinus communis | castor oil |
| Saccharum officinarum | sugar cane |
| Secale cereale | rye |
| Solanum tuberosum | potato |
| Sorghum bicolor (S. vulgare) | sorghum |
| Theobroma cacao | cocoa |
| Trifolium pratense | red clover |
| Triticum aestivum | wheat |
| Triticum durum | durum wheat |
| Vicia faba | horse bean |
| Vitis vinifera | grapevine |
| Zea mays | corn |

The extend the spectrum of action and to active synergistic effects, the novel compounds I can be mixed and applied together with many representatives of other groups of herbicides or growth regulators. Examples of suitable mixing partners are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives, quinolinecarboxylic acid derivatives, sulfonylureas, aryloxy- and hetaryloxyphenoxypropionic acids and the salts, esters and amides thereof, and others.

It may also be beneficial to apply the compounds I, alone or in combination with other herbicides, mixed together with other crop protection agents, for example with agents for controlling pests or phytopathogenic fungi or bacteria. Also of interest is the miscibility with mineral salt solutions which can be employed to eliminate deficiencies in nutrients and trace elements. It is also possible to add non-phytotoxic oils and oil concentrates.

SYNTHESIS EXAMPLES

Dimethyl 3-tert-butylaminocarbonylisoxazole-4,5-dicarboxylate

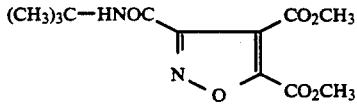

18.2 g (0.8 mol) of triethylamine were added dropwise at 0° C. to 24.0 g (0.15 mol) of tert-butylcarbamoylformohydroxamyl chloride and 21.3 g (0.15 mol) of dimethyl acetylenedicarboxylate in 300 ml of tetrahydrofuran. The mixture was stirred at room temperature for 5 hours and refluxed for 2 hours. The solvent was then stripped off under reduced pressure, and the residue was taken up in 300 ml of dichloromethane and extracted twice with 100 ml of dilute HCl each time and once with 100 ml of water. The organic phase was dried over magnesium sulfate, the dichloromethane was stripped off in a rotary evaporator, and the crude product was purified by column chromatography (SiO$_2$; cyclohexane/ethyl acetate 5:1), resulting in dimethyl 3-tert-butylaminocarbonylisoxazole-4,5-dicarboxylate in pure form.

Methyl 3-tert-butylaminocarbonyl-5-cyclopropylaminocarbonylisoxazole-4-carboxylate

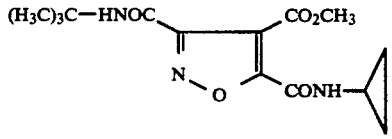

0.75 g (l3.1 mmol) of cyclopropylamine was added dropwise at 20° C., with cooling, to a solution of 2.5 g (8.8 mmol) of dimethyl 3-tert-butylaminocarbonylisoxazole-4,5-dicarboxylate in 50 ml of dry methanol, and the mixture was stirred at room temperature for 20 hours. The solvents were stripped off under reduced pressure, and the residue was taken up in methyl tert-butyl ether and extracted with dilute HCl and once with water. The organic phase was then dried over magnesium sulfate, and the solution was evaporated. The resulting methyl3-tert-butylaminocarbonyl-5-cyclopropylaminocarbonylisoxazole-4-carboxylate was purified by column chromatography (SiO$_2$; cyclohexane/ethyl acetate 4:1).

3-tert-Butylaminocarbonyl-5-cyclopropylaminocarbonylisoxazole-4-carboxylic acid

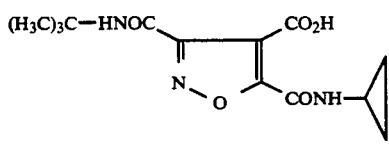

0.26 g (6.5 mmol) of sodium hydroxide in 20 ml of water was added dropwise at 5° to 10° C. to a solution of 1.0 g (3.2 mmol) of methyl 3-tert-butylaminocarbonyl-5-cyclopropylaminocarbonylisoxazole- 4-carboxylate in 50 ml of methanol. After stirring at room temperature for 12 hours, the solvent was removed, the residue was taken up in 50 ml of water and the mixture was adjusted to pH =8 to 9 and extracted twice with diethyl ether. The aqueous phase was then acidified to pH=2 and extracted with ethyl acetate, and the combined organic phases were dried over magnesium sulfate and evaporated.

The compounds listed in Table 1 were prepared analogously.

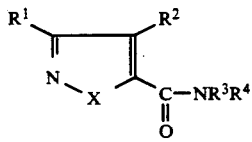

where
X is oxygen or sulfur;
R$^1$ is halogen,
C$_1$–C$_4$-alkylaminocarbonyl, di-C$_1$–C$_3$-alkylaminocarbonyl or cyclopropylaminocarbonyl;
R$^2$ is COOR$^5$, where
R$^5$ is hydrogen; C$_1$–C$_6$-alkyl which can carry 1 to 5 halogens and/or up to three hydroxyl and/or C$_1$–C$_4$-alkoxy groups;
R$^3$ is hydrogen or
C$_1$–C$_6$-alkyl;
R$^4$ is hydrogen;
C$_1$–C$_6$-alkyl which can carry one to three of the following: halogen, cyano, C$_1$–C$_4$-alkoxy, partially or completely halogenated C$_1$–C$_4$-alkoxy, C$_1$–C$_4$-alkylthio, partially or completely halogenated C$_1$–C$_4$-alkylthio, di-C$_1$–C$_4$-alkylamino, C$_3$–C$_8$-cycloalkyl or phenyl, it being possible for the latter in turn to carry one to three of the following: halo-

TABLE 1
Isoxazole-5-carboxamides

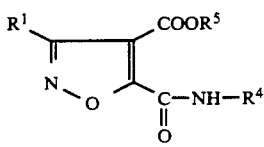

| Nr. | R$^1$ | R$^5$ | R$^4$ | mp [°C.]/$^1$H—NMR (250 MHZ; CDCl$_3$ oder DMSO, δ in ppm) |
|---|---|---|---|---|
| 1.001 | t-Butylaminocarbonyl | Methyl | Cyclopropyl | 152–154 |
| 1.002 | t-Butylaminocarbonyl | Ethyl | Cyclopropyl | 125–129 |
| 1.003 | t-Butylaminocarbonyl | Ethyl | t-Butyl | 1.37(t; 3H), 1.46(s; 9H), 1.47(s; 9H), 4.40(9; 2H) |
| 1.004 | t-Butylaminocarbonyl | H | Cyclopropyl | 135–138 |
| 1.005 | Dimethylaminocarbonyl | Ethyl | Cyclopropyl | 0.60–0.94(m; 4H), 2.92 und 3.14(2s; 2×3H), 9.58(6s; 1H, NH) |
| 1.006 | t-Butylaminocarbonyl | H | t-Butyl | 157–159 |
| 1.007 | Methylethylaminocarbonyl*) | Ethyl | Cyclopropyl | 0.58–0.96(m; 4H), 4.35(q; 2H), 9.58(bs; 1H, NH) |
| 1.008 | Dimethylaminocarbonyl | H | Cyclopropyl | 205–207 |
| 1.009 | Methylethylaminocarbonyl*) | Ethyl | t-Butyl | 1.50(s; 9H), 4.36(q, 2H); 9.34(bs; 1H, NH) |
| 1.010 | Br | CH$_3$ | C(CH$_3$)$_2$C≡CH | 92–102 |
| 1.011 | Br | CH$_3$ | Cyclopropyl | 109–113 |
| 1.012 | Br | H | C(CH$_3$)$_2$C≡CH | 3.25(d; 1H), 9.55(s, 1H) |
| 1.013 | Br | H | Cyclopropyl | 160–161 |
| 1.014 | Br | CH$_3$ | tert.-Butyl | 122–123 |
| 1.015 | Br | CH$_3$ | m-CF$_3$—C$_6$H$_4$ | 119–120 |
| 1.016 | Br | H | tert.-Butyl | 129–133 |
| 1.017 | Br | H | Isopropyl | 126–128 |
| 1.018 | Br | H | C$_6$H$_5$ | 203–204 |
| 1.019 | Cl | CH$_3$ | Cyclopropyl | 73–76 |
| 1.020 | Cl | H | Cyclopropyl | 152–153 |
| 1.021 | Cl | H | tert.-Butyl | 152–156 |

*)mixture of two retomers

We claim:
1. An isoxazole- or isothiazole-5-carboxamide of the formula I gen, cyano, nitro, C$_1$–C$_4$-alkyl, partially or completely halogenated C$_1$–C$_4$-alkyl, C$_1$–C$_4$-alkoxy, partially or completely halogenated C$_1$–C$_4$-alkoxy or C$_1$–C$_4$-alkylthio;
C$_3$–C$_8$-cycloalkyl which can carry one to three of the following: halogen, nitro, cyano, C$_1$–C$_8$-alkyl, partially or completely halogenated $C_1$-$C_6$-alkyl, $C_1$-$C_4$-alkoxy or partially or completely halogenated $C_1$-$C_4$-alkoxy;

$C_3$-$C_6$-alkenyl or $C_3$-$C_6$-alkynyl, each of which can be substituted one to three times by halogen and/or once by phenyl which in turn can carry one to three of the following groups: $C_1$-$C_4$-alkyl;

phenyl which can carry one to four of the following groups: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, nitro, cyano, formyl, $C_2$-$C_4$-alkanyl, $C_2$-$C_4$-haloalkanoyl or $C_1$-$C_4$-alkoxycarbonyl;

and the environmentally compatible salts of the compound I.

2. A carboxamide of the formula I as defined in claim 1, where X is oxygen and $R^3$ is hydrogen.

3. A herbicidal composition containing inert carriers and a herbicidal amount of at least one carboxamide of the formula I as defined in claim 1.

4. A method for controlling unwanted plant growth, which comprises treating the unwanted plants and/or their habitat with a herbicidal amount of a carboxamide of the formula I as defined in claim 1.

5. A carboxamide of the formula I as defined in claim 1, wherein X is oxygen, $R^1$ is bromine, $R^2$ and $R^3$ are each hydrogen, $R^4$ is $mCF_3$—$C_6H_4$ and $R^5$ is $CH_3$.

6. A carboxamide of the formula I as defined in claim 1, wherein $R^4$ is t-butyl.

7. A carboxamide of the formula I as defined in claim 1, wherein $R^1$ is Br, $R^2$ is $COOR^5$, where $R^5$ is hydrogen and $R^4$ is t-butyl.

* * * * *

UNITED STATES PATENT AND TRADEMARK OFFICE
CERTIFICATE OF CORRECTION

PATENT NO. : 5,203,907
DATED : April 20, 1993
INVENTOR(S) : Maywald et al.

It is certified that error appears in the above-identified patent and that said Letters Patent is hereby corrected as shown below:

Claim 1, column 35, line 14: "$C_2$-$C_4$-alkanyl" should read --$C_2$-$C_4$-alkanoyl--.

Signed and Sealed this

Fifteenth Day of February, 1994

*Attest:*

BRUCE LEHMAN

*Attesting Officer*  *Commissioner of Patents and Trademarks*